(12) United States Patent
Jung

(10) Patent No.: US 9,755,153 B2
(45) Date of Patent: Sep. 5, 2017

(54) ORGANIC COMPOUND AND ORGANIC LIGHT EMITTING DIODE DEVICE INCLUDING THE SAME

(71) Applicant: SAMSUNG DISPLAY CO., LTD., Yongin, Gyeonggi-Do (KR)

(72) Inventor: Ji Yun Jung, Seoul (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 288 days.

(21) Appl. No.: 14/553,022

(22) Filed: Nov. 25, 2014

(65) Prior Publication Data

US 2016/0028018 A1    Jan. 28, 2016

(30) Foreign Application Priority Data

Jul. 24, 2014 (KR) .................. 10-2014-0094259

(51) Int. Cl.
*H01L 51/00* (2006.01)
*C09K 11/06* (2006.01)
*C07D 471/04* (2006.01)
*H01L 51/50* (2006.01)

(52) U.S. Cl.
CPC ........ *H01L 51/0055* (2013.01); *C07D 471/04* (2013.01); *C09K 11/06* (2013.01); *H01L 51/0058* (2013.01); *H01L 51/0067* (2013.01); *H01L 51/0072* (2013.01); *H01L 51/5012* (2013.01); *H01L 51/5072* (2013.01); *H01L 2251/308* (2013.01)

(58) Field of Classification Search
None
See application file for complete search history.

(56) References Cited

U.S. PATENT DOCUMENTS

2009/0118292 A1* 5/2009 Deng .................. C07D 487/04
514/248

FOREIGN PATENT DOCUMENTS

| JP | 10-017860 A | 1/1998 |
| JP | 11-087067 A | 3/1999 |
| JP | 11-345686 A | 12/1999 |
| KR | 10-2001-0015513 A | 2/2001 |
| KR | 10-2011-0095482 A | 8/2011 |

* cited by examiner

*Primary Examiner* — J. L. Yang
(74) *Attorney, Agent, or Firm* — Lee & Morse, P.C.

(57) ABSTRACT

A compound, an organic light emitting diode device, and a display device, the compound being represented by the following Chemical Formula 1:

[Chemical Formula 1]

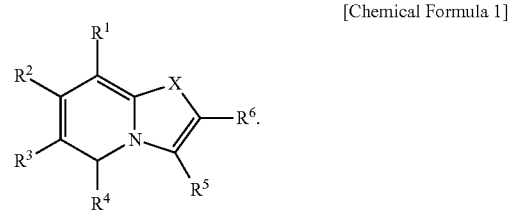

14 Claims, 3 Drawing Sheets

ORGANIC COMPOUND AND ORGANIC LIGHT EMITTING DIODE DEVICE INCLUDING THE SAME

CROSS-REFERENCE TO RELATED APPLICATION

Korean Patent Application No. 10-2014-0094259 filed on Jul. 24, 2014, in the Korean Intellectual Property Office, and entitled: "Organic Compound and Organic Light Emitting Diode Device Including the Same," is incorporated by reference herein in its entirety.

BACKGROUND

1. Field

Embodiments relate to an organic compound and an organic light emitting diode device including the same.

2. Description of the Related Art

Recent trends toward lightweight and thin personal computers and televisions sets also require lightweight and thin display devices, and flat panel displays satisfying such requirements are being substituted for cathode ray tubes (CRTs). However, the LCD is a passive display device, an additional backlight as a light source is needed, and the LCD may have a slow response time and a narrow viewing angle.

An organic light emitting diode (OLED) device has been considered as a display device that has merits such as a wide viewing angle, outstanding contrast, and a fast response time.

In the organic light emitting diode device, electrons injected from one electrode and holes injected from another electrode may be combined with each other in an emission layer, thereby generating excitons, and energy may be outputted from the excitons to thereby emit light.

The above information disclosed in this Background section is only for enhancement of understanding of the background therefore it may contain information that does not form the prior art that is already known in this country to a person of ordinary skill in the art.

SUMMARY

Embodiments are directed to an organic compound and an organic light emitting diode device including the same.

The embodiments may be realized by providing a compound represented by the following Chemical Formula 1:

[Chemical Formula 1]

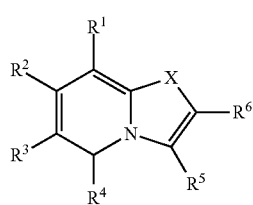

wherein, in Chemical Formula 1, X is CRR' or NR, R and R' are each independently hydrogen, heavy hydrogen, a substituted or unsubstituted C6 to C30 aryl group, or a substituted or unsubstituted C2 to C30 heteroaryl group, $R^1$ to $R^4$ are each independently hydrogen, heavy hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C1 to C30 amine group, or a substituted or unsubstituted silyl group, $R^5$ is hydrogen, heavy hydrogen, a substituted or unsubstituted C6 to C50 aryl group, a substituted or unsubstituted C2 to C50 heteroaryl group, or a substituted or unsubstituted fused ring-containing group, and $R^6$ is hydrogen, heavy hydrogen, a substituted or unsubstituted C6 to C50 aryl group, a substituted or unsubstituted C2 to C50 heteroaryl group, a substituted or unsubstituted C1 to C30 amine group, or a substituted or unsubstituted fused ring-containing group.

The compound represented by Chemical Formula 1 may be represented by the following Chemical Formula 2:

[Chemical Formula 2]

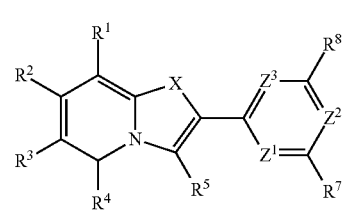

wherein, in Chemical Formula 2, $Z^1$ to $Z^3$ may each independently be CR" or N, and at least one of $Z^1$ to $Z^3$ is N, R" may be hydrogen, heavy hydrogen, a substituted or unsubstituted C6 to C30 aryl group, or a substituted or unsubstituted C2 to C30 heteroaryl group, $R^7$ and $R^8$ may each independently be hydrogen, heavy hydrogen, a substituted or unsubstituted C6 to C50 aryl group, a substituted or unsubstituted C2 to C50 heteroaryl group, or a substituted or unsubstituted fused ring-containing group, and X and $R^1$ to $R^5$ may be the same as defined with respect to Chemical Formula 1.

At least one of $R^5$, $R^7$, and $R^8$ may include the fused ring-containing group.

The fused ring-containing group may include a moiety represented by one of the following Chemical Formulae "a" to "s":

[Chemical Formula a]

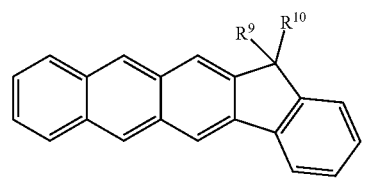

[Chemical Formula b]

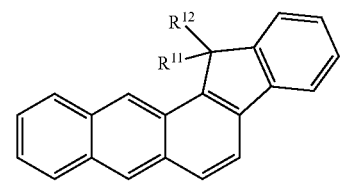

-continued
[Chemical Formula c]
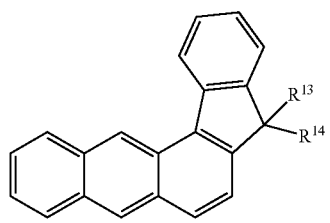
[Chemical Formula d]
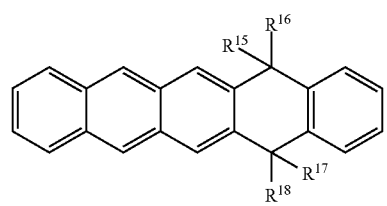
[Chemical Formula e]
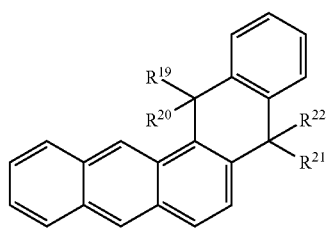
[Chemical Formula f]
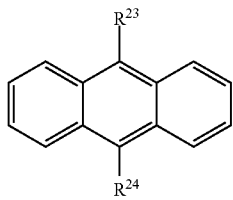
[Chemical Formula g]
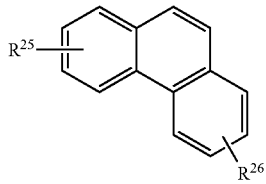
[General Formula h]
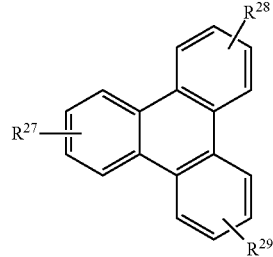
[General Formula i]
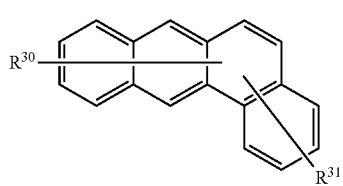
[General Formula j]
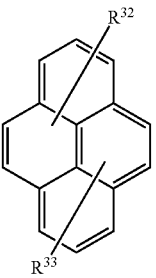
[General Formula k]
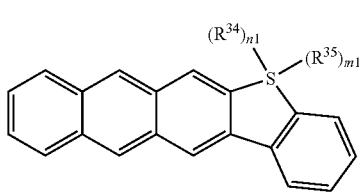
[General Formula l]
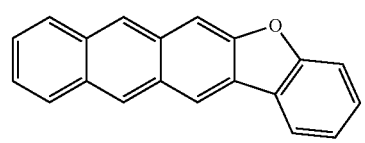
[General Formula m]
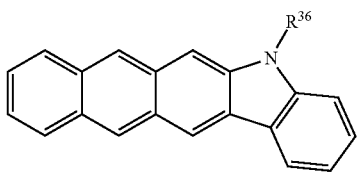
[General Formula n]
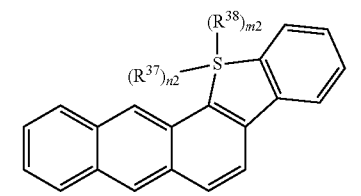
[General Formula o]
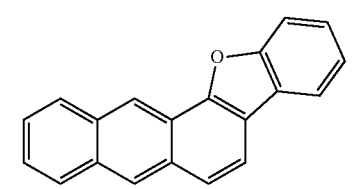
[General Formula p]
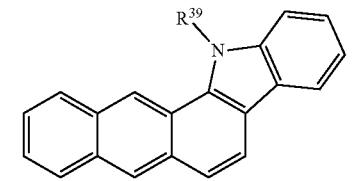

[General Formula q]

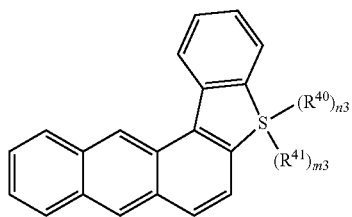

[General Formula r]

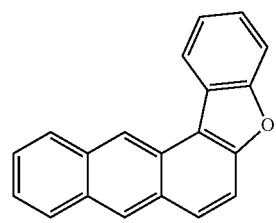

[General Formula s]

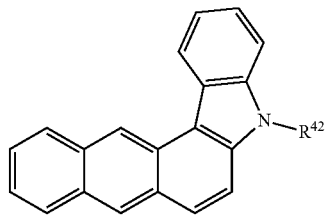

wherein, in Chemical Formulae "a" to "s", $R^9$ to $R^{42}$ may each independently be hydrogen, heavy hydrogen, a substituted or unsubstituted C1 to C30 alkyl group, a substituted or unsubstituted C6 to C30 aryl group, or a substituted or unsubstituted C2 to C30 heteroaryl group, and n1, n2, n3, m1, m2, and m3 may each independently be 0 or 1.

X may be NR, and R may be a substituted or unsubstituted C6 to C30 aryl group.

$R^1$, $R^3$, and $R^4$ may be hydrogen, and $R^2$ may be hydrogen or a substituted or unsubstituted C6 to C50 aryl group.

$R^2$ may be hydrogen, a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, or a substituted or unsubstituted pyrenyl group.

The compound represented by Chemical Formula 1 may be represented by one of the following Chemical Formulae 3 to 51:

3

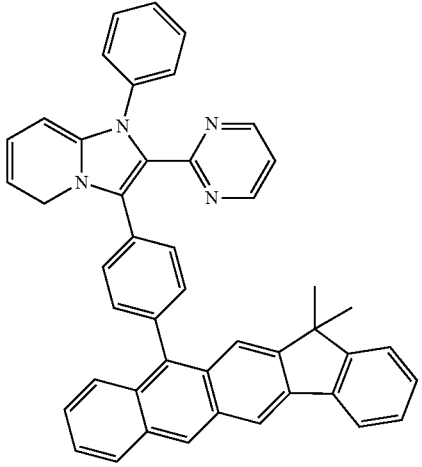

4

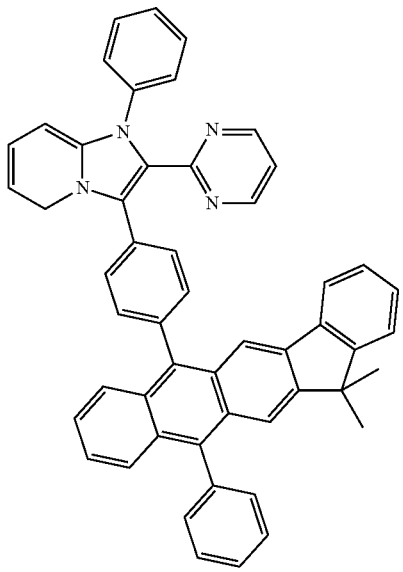

5

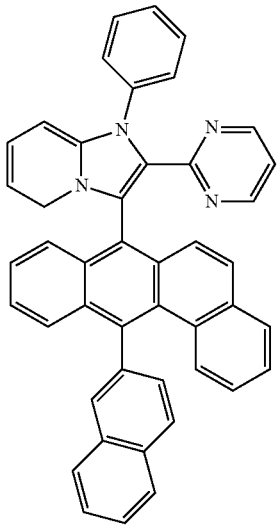

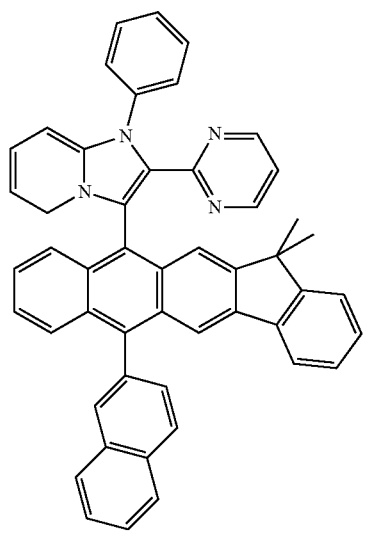
6
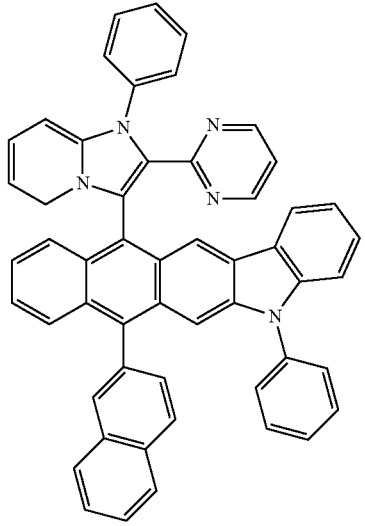
9
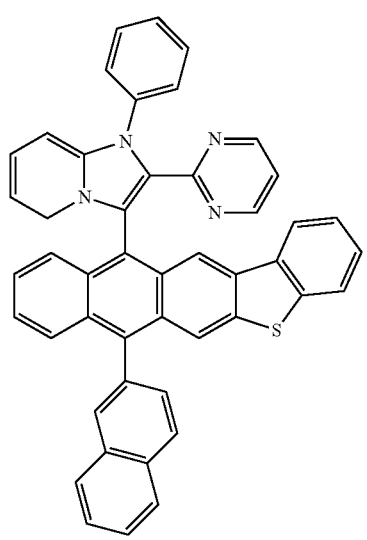
7
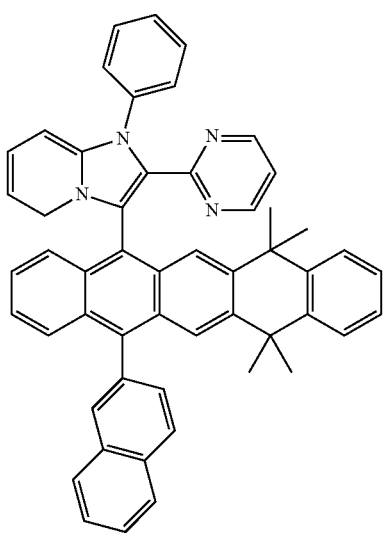
10
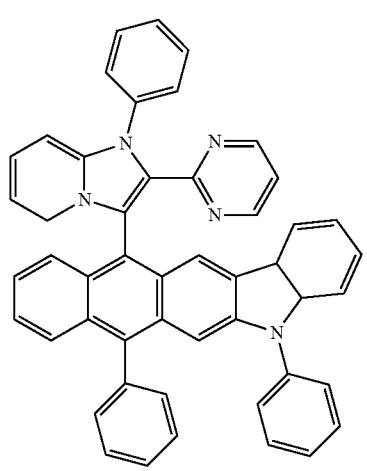
8
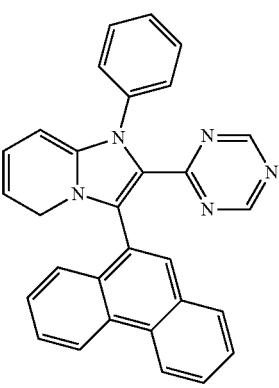
11

12
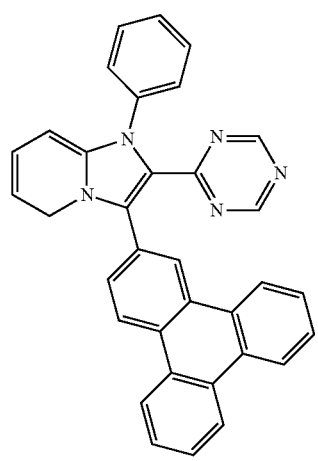
13
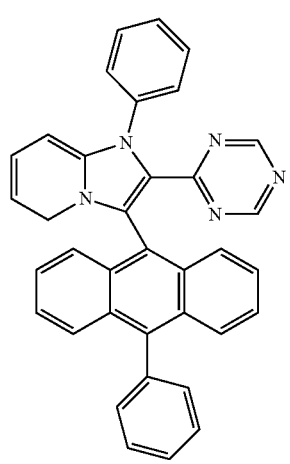
14
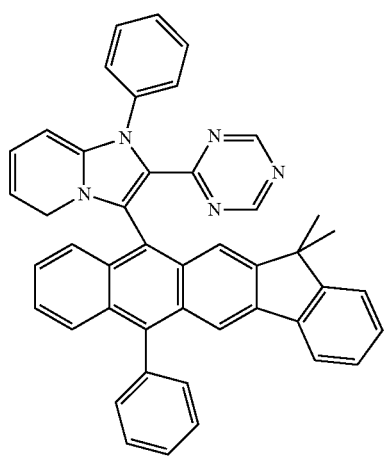
15
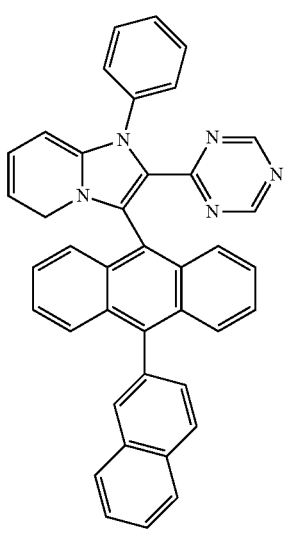
16
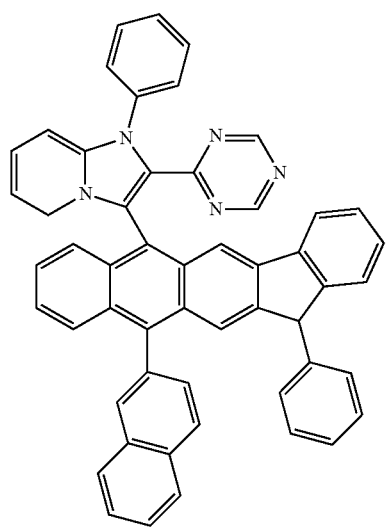
17
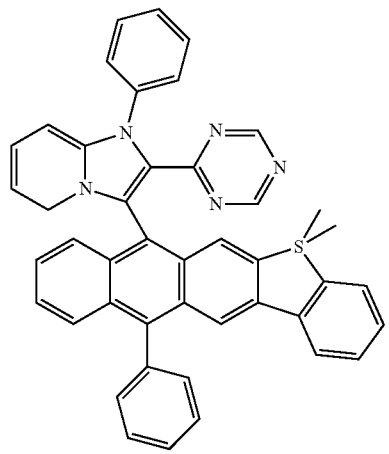

11
-continued
18
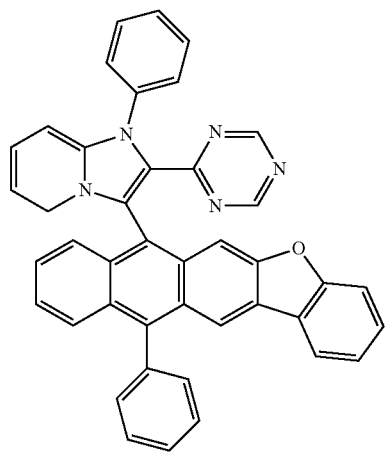
19
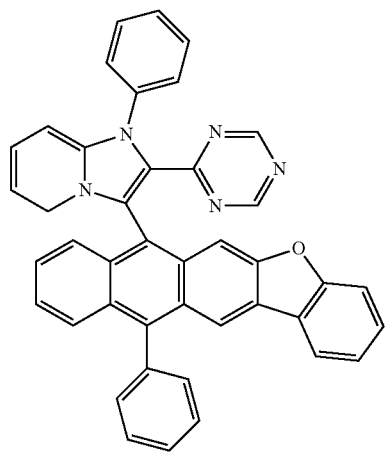
20
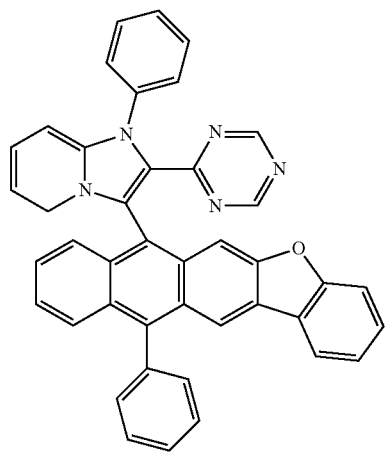
12
-continued
21
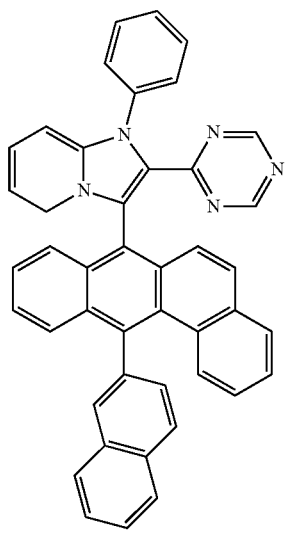
22
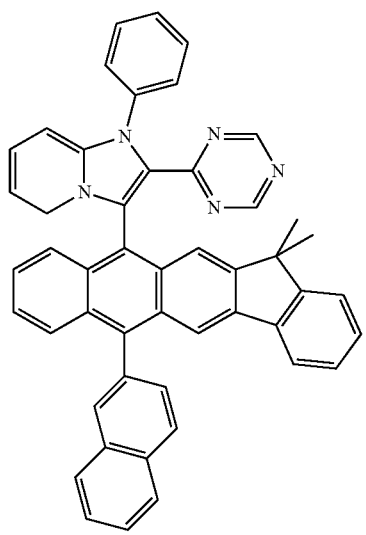
23
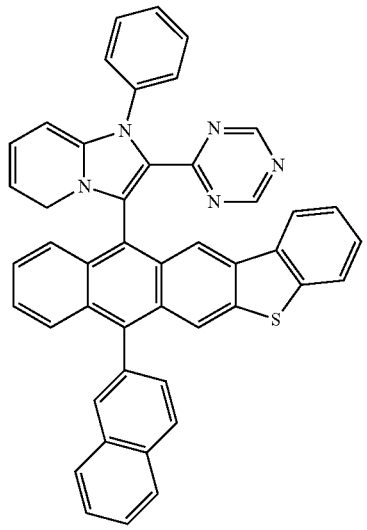

24
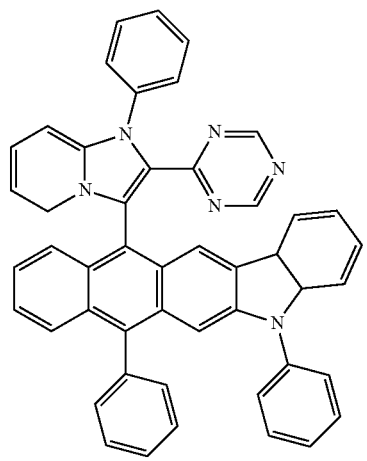
25
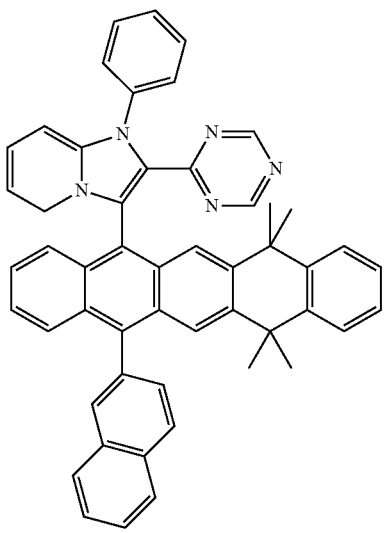
27
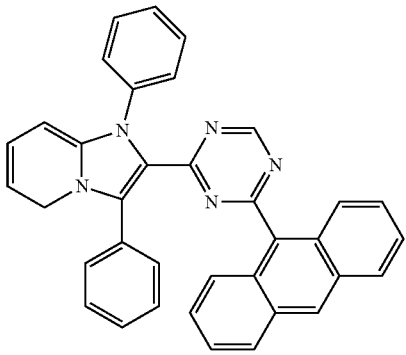
28
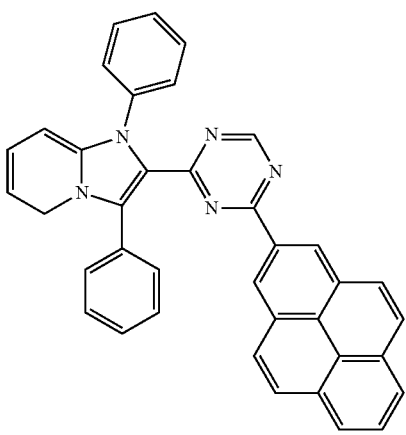
29
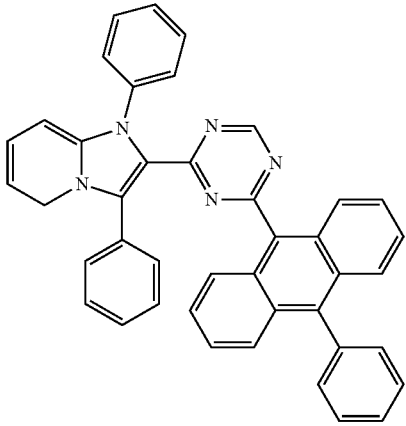

30
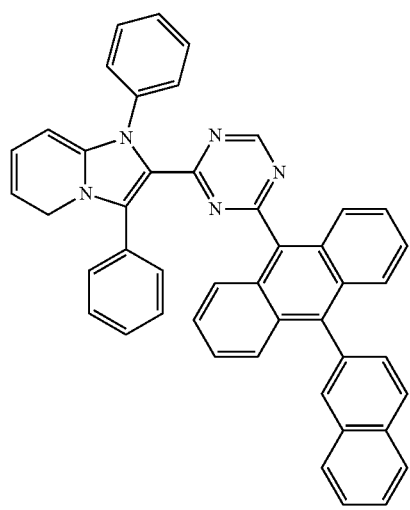
31
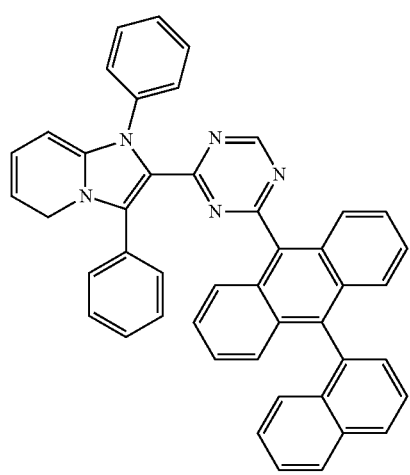
32
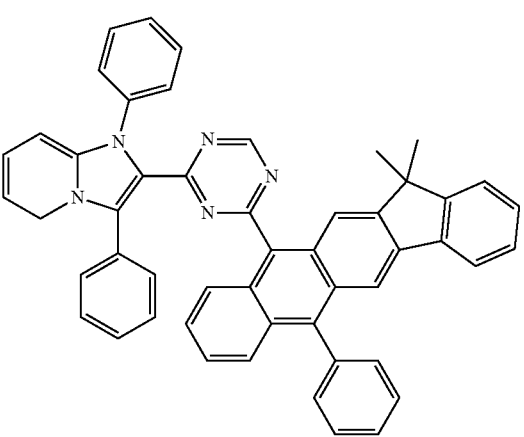
33
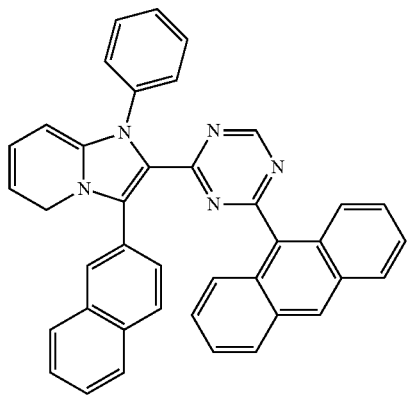
34
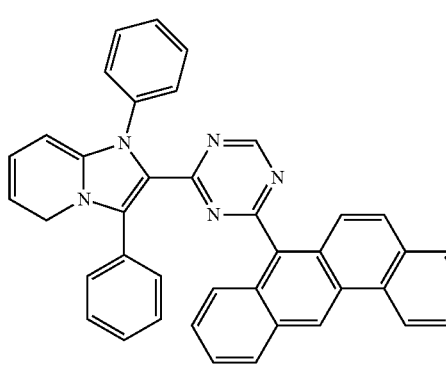
35
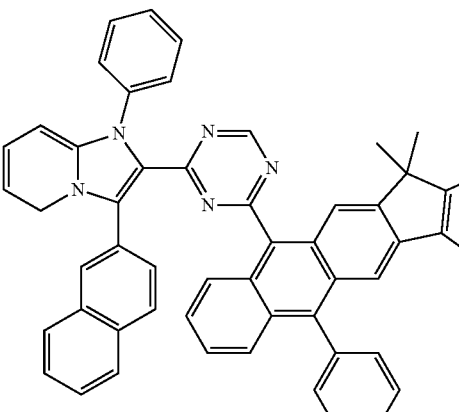
36
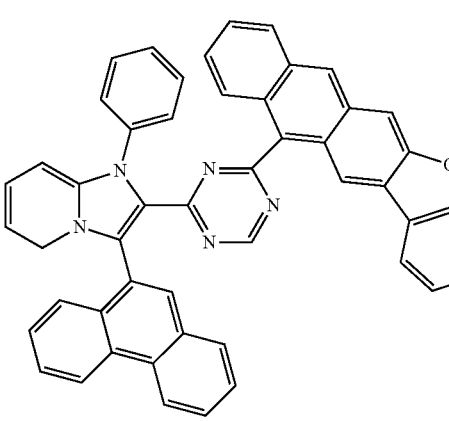

37
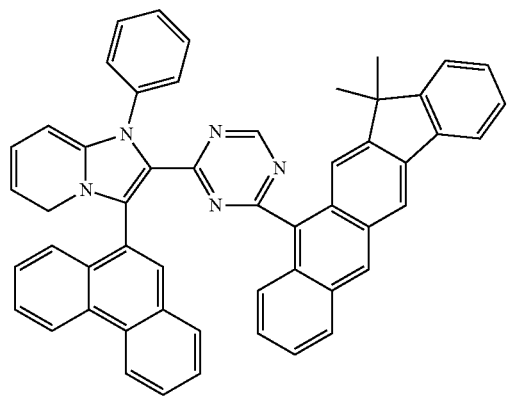
38
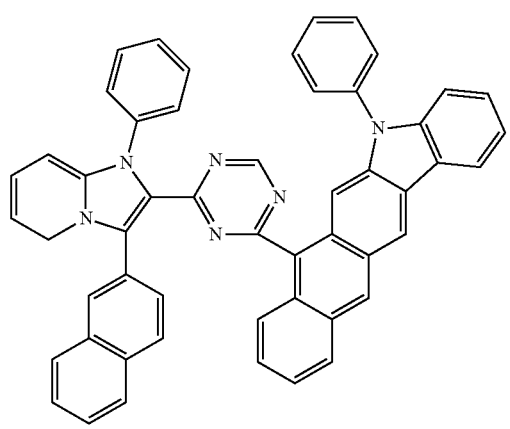
39
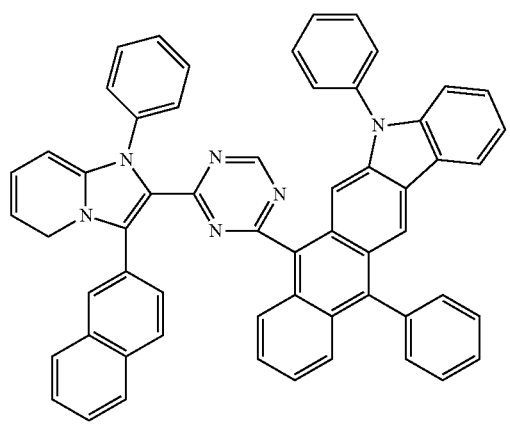
40
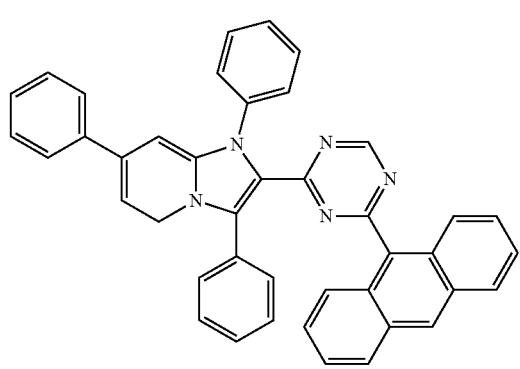
41
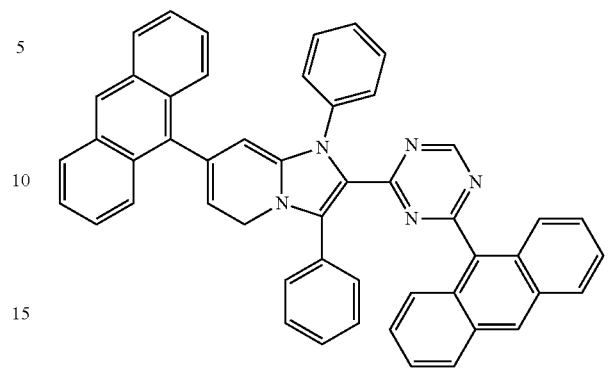
42
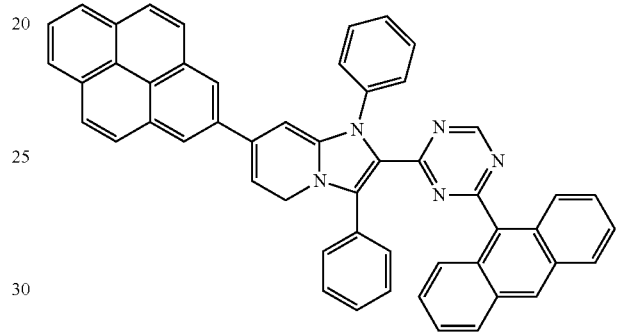
43
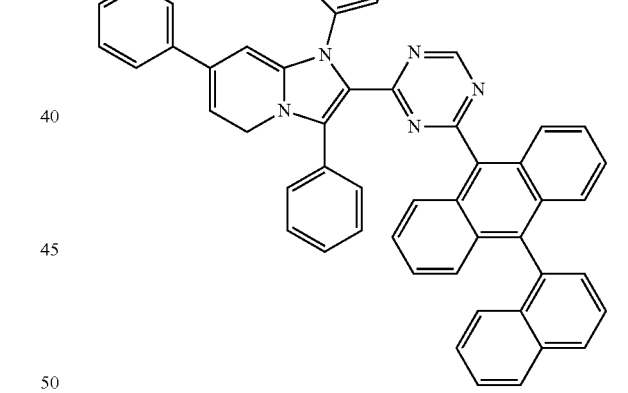
44
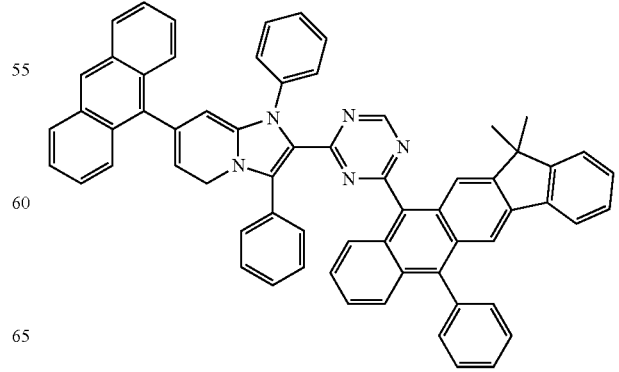

45

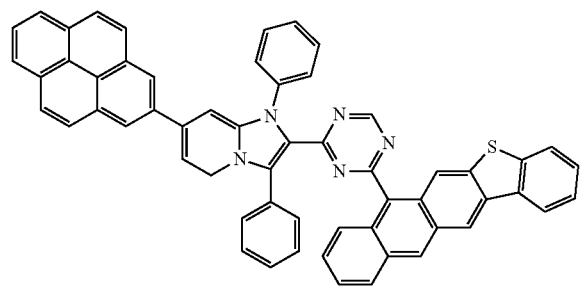

46

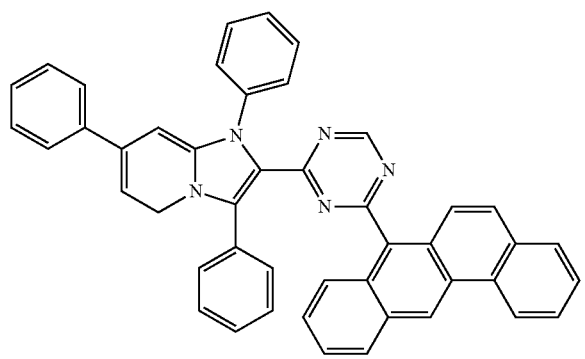

47

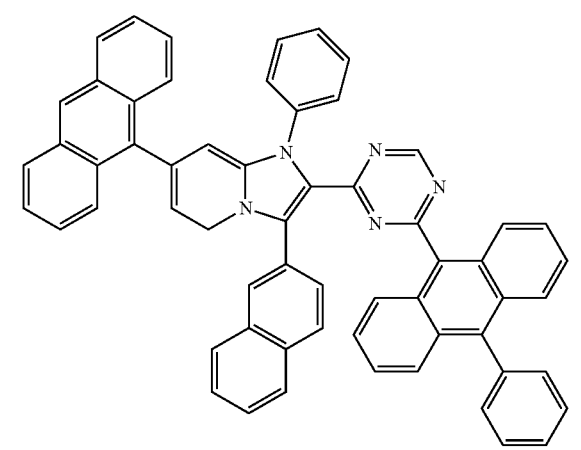

48

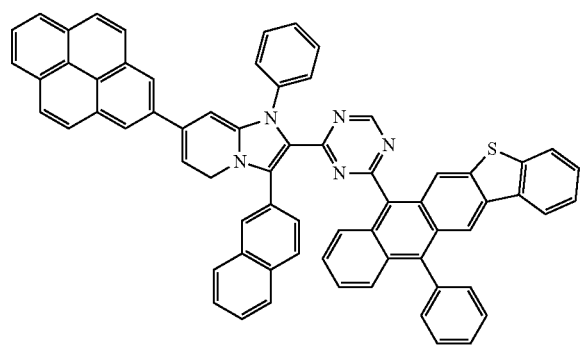

49

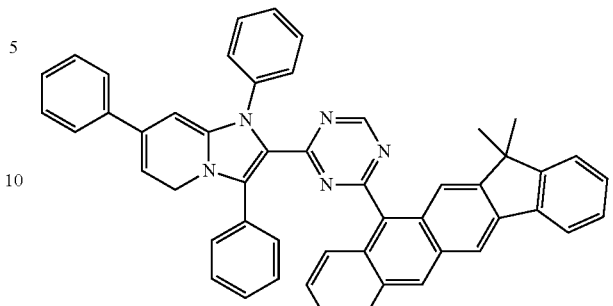

50

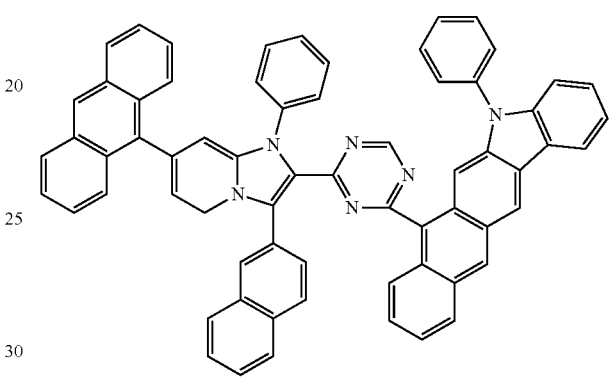

51

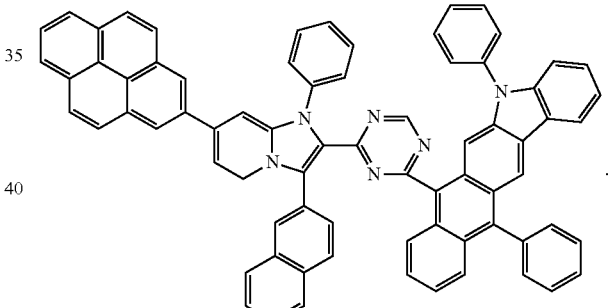

The embodiments may be realized by providing an organic light emitting diode device including an anode; a cathode; and an organic layer between the anode and the cathode, wherein the organic layer contains the compound according to an embodiment.

The organic layer may include an electron injection layer, an electron transport layer, a hole injection layer, a hole transport layer, or an emission layer.

The organic layer may include an electron injection layer or an electron transport layer.

The organic layer may include the electron transport layer, the electron transport layer may include the compound, and the electron transport layer may further include a metal-containing material.

The metal-containing material may include a Li complex.

The embodiments may be realized by providing a display device including the organic light emitting diode device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
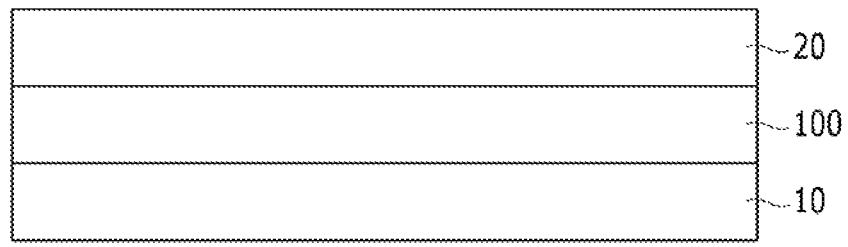
FIGS. 1 to 3 illustrate a structure of an organic light emitting diode device according to an exemplary embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

It will be understood that when an element such as a layer, film, region, or substrate is referred to as being "on" another element, it can be directly on the other element or intervening elements may also be present. In contrast, when an element is referred to as being "directly on" another element, there are no intervening elements present.

In this specification, when a target element is described as being "substituted", this indicates that at least one hydrogen atom is substituted with a substituent selected from a set consisting of heavy hydrogen (i.e., deuterium), a C1 to C30 alkyl group, a C6 to C30 aryl group, a C2 to C30 heteroaryl group, a C1 to C30 alkoxy group, a C2 to C30 alkenyl group, a C6 to C30 aryloxy group, a C1 to C30 silyloxy group, a C1 to C30 acyl group, a C2 to C30 acyloxy group, a C2 to C30 heteroaryloxy group, a C1 to C30 sulfonyl group, a C1 to C30 alkylthiol group, a C6 to C30 arylthiol group, a C1 to C30 heterocyclothiol group, a C1 to C30 phosphate amide group, a C3 to C30 silyl group, $NR_aR_b$ (herein, $R_a$ and $R_b$ indicate substitutes independently selected from hydrogen atoms, the C1 to C30 alkyl group, and the C6 to C30 aryl group), a carboxyl group, a halogen group, a cyano group, a nitro group, an azo group, a fluorine group, and a hydroxyl group, unless otherwise defined.

In addition, two adjacent substituents of the substituted C1 to C30 alkyl group, C6 to C30 aryl group, C2 to C30 heteroaryl group, C1 to C30 alkoxy group, C2 to C30 alkenyl group, C6 to C30 aryloxy group, C1 to C30 silyloxy group, C1 to C30 acyl group, C2 to C30 acyloxy group, C2 to C30 heteroaryloxy group, C1 to C30 sulfonyl group, C1 to C30 alkylthiol group, C6 to C30 arylthiol group, C1 to C30 heterocyclothiol group, C1 to C30 phosphate amide group, C3 to C30 silyl group, $NR_aR_b$ (herein, $R_a$ and $R_b$ indicate substitutes independently selected from hydrogen atoms, the C1 to C30 alkyl group, and the C6 to C30 aryl group), carboxyl group, halogen group, cyano group, nitro group, azo group, fluorine group, or hydroxyl group may be fused to form a ring.

As used herein, the term "fused ring" indicates a ring formed by the two adjacent substituents that are fused, unless otherwise defined.

Further, in this specification, the prefix "hetero" indicates that 1 to 3 heteroelements selected from a group consisting of N, O, S, and P are contained in one ring, and the other elements of the ring are carbon elements, unless otherwise defined.

In this specification, the phrase "combination thereof" indicates coupling of two or more substituents using an adapter, or coupling of two or more substituents by being condensed.

In this specification, the term "organic layer" is a comprehensive term indicating a layer containing an organic material, for example, a multilayer including at least one layer containing an inorganic material, a metallic complex, and the like as well as the organic material.

The definitions of main ones of the groups used in chemical formulae of the embodiments will be described as follows (the carbon number for defining substituents is unrestrictive and does not restrict the characteristics of the substituents).

An unsubstituted C1 to C30 alkyl group may be a linear or branched type, and a non-limited example of the alkyl group may include methyl, ethyl, propyl, iso-butyl, sec-butyl, pentyl, iso-amyl, hexyl, heptyl, octyl, nonyl, dodecyl, or the like.

An unsubstituted C2 to C30 alkenyl group indicates that at least one carbon double bond is contained at the middle or the distal end of the unsubstituted alkyl group. An example of the alkenyl group includes ethenyl, propenyl, or the like.

An unsubstituted C2 to C30 alkynyl group indicates that at least one carbon triple bond is contained at the middle or the distal end of the unsubstituted alkyl group. An example of the alkynyl group may include acetylene, acetylene, propyne, phenylacetylene, naphthylacetylene, iso-propylacetylene, t-butylacetylene, diphenyl acetylene, or the like.

An unsubstituted C3 to C30 cycloalkyl group indicates an annular alkyl group having a carbon number in a range from 3 to 30.

An unsubstituted C1 to C30 alkoxy group indicates a group having the structure of "—OA" (herein, "A" indicates an unsubstituted C1 to C30 alkyl group), and a non-limited example of the alkoxy group includes methoxy, ethoxy, propoxy, iso-propyloxy, butoxy, pentoxy, or the like.

An unsubstituted C6 to C30 aryl group indicates a carbocycle aromatic system having at least one ring. In the case of having two or more rings, these may be connected to each other through a single bond or by being fused with each other. The terms "aryl" includes an aromatic system such as phenyl, naphthyl, anthracenyl, or the like. An example of the unsubstituted C6 to C30 aryl group may include one selected from a set consisting of a phenyl group, a biphenyl group, a tolyl group, a naphthyl group, an anthracenyl group, a terphenyl group, a naphthacenyl group, a phenanthrenyl group, a pyrenyl group, a diphenylanthracenyl group, a dinaphthylanthracenyl group, a chrycenyl group, a triphenylenyl group, a perylenyl group, a pentacenyl group, a bromophenyl group, a hydroxyphenyl group, a stilbene group, an azobenzene group, and a ferrocenyl group.

An unsubstituted C2 to C30 heteroaryl group has 1, 2, or 3 heteroatoms selected from a set consisting of N, O, S, and P. In the case of having two or more rings, these may be connected to each other through a single bond or by being fused with each other. An example of the unsubstituted C2 to C30 heteroaryl group includes a pyrazolyl group, an imidazolyl group, an oxazolyl group, a triazolyl group, a triazinyl group, a triazolyl group, a tetrazolyl group, an oxadiazole group, a thiadiazole group, a pyridinyl group, a pyridazinyl group, a pyrimidinyl group, a carbazole group, an indolyl group, a quinolyl group, an isoquinolyl group, a thiophene group, a dibenzothiophene group, a dibenzofuran group, and a benzimidazolyl group.

An unsubstituted C6 to C30 aryloxy group is a group represented by —OA1. Herein, A1 is substantially the same functional group as that of the C6 to C30 aryl group except for the carbon number. An example of the aryloxy group may include a phenoxy group.

An unsubstituted C6 to C30 arylthiol group is a group represented by —SA1. Herein, A1 is substantially the same functional group as that of the C6 to C30 aryl group except for the carbon number. An example of the arylthiol group may include a benzenethiol group, a naphthylthiol group, or the like.

In this specification, "hole characteristic" indicates a characteristic serving to facilitate the injection of holes into an emission layer and the movement of the holes, the holes being formed in an anode by having a conductivity characteristic according to a HOMO level. Specifically, the hole characteristic may be similar to a characteristic of pushing electrons.

Further, in this specification, "electron characteristic" indicates a characteristic serving to facilitate the injection of electrons into an emission layer and the movement of the electrons, the electrons being formed in a cathode by having the conductivity characteristic according to the HOMO level. Specifically, the hole characteristic may be similar to a characteristic of pulling electrons.

Hereinafter, exemplary embodiments will be described in detail.

An organic compound according to a first exemplary embodiment may be represented by the following Chemical Formula 1.

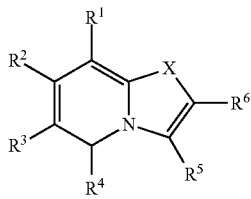

[Chemical Formula 1]

In Chemical Formula 1,

X may be CRR' or NR,

R and R' may each independently be hydrogen, heavy hydrogen, a substituted or unsubstituted C6 to C30 aryl group, or a substituted or unsubstituted C2 to C30 heteroaryl group, $R^1$ to $R^4$ may each independently be hydrogen, heavy hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C1 to C30 amine group, or a substituted or unsubstituted silyl group, $R^5$ may be hydrogen, heavy hydrogen, a substituted or unsubstituted C6 to C50 aryl group, a substituted or unsubstituted C2 to C50 heteroaryl group, or a substituted or unsubstituted fused ring-containing group, and $R^6$ may be hydrogen, heavy hydrogen, a substituted or unsubstituted C6 to C50 aryl group, a substituted or unsubstituted C2 to C50 heteroaryl group, a substituted or unsubstituted C1 to C30 amine group, or a substituted or unsubstituted fused ring-containing group.

In an implementation, the compound represented by the Chemical Formula 1 may have various energy band gaps by introducing various substituents.

Hole-transfer capability or the electron-transfer capability may be improved by employing a compound having an energy level that is appropriately adjusted according to a substituent thereof in the organic light emitting diode device, thereby accomplishing an outstanding effect in efficiency and a driving voltage and high electrochemical and thermal stability. Accordingly, it is possible to extend a lifespan when the organic light emitting diode device is driven.

An organic compound according to a second exemplary embodiment may be represented by the following Chemical Formula 2. For example, the compound represented by Chemical Formula 1 may be represented by Chemical Formula 2.

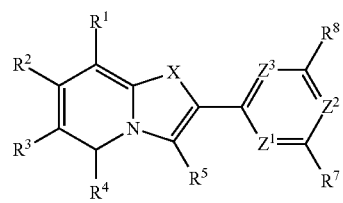

[Chemical Formula 2]

In Chemical Formula 2,

X and $R^1$ to $R^5$ may be the same as defined with respect to Chemical Formula 1, $Z^1$ to $Z^3$ may each independently be CR" or N, and at least one of $Z^1$ to $Z^3$ may be N, R" may be hydrogen, heavy hydrogen, a substituted or unsubstituted C6 to C30 aryl group, or a substituted or unsubstituted C2 to C30 heteroaryl group, and $R^7$ and $R^8$ may each independently be hydrogen, heavy hydrogen, a substituted or unsubstituted C6 to C50 aryl group, a substituted or unsubstituted C2 to C50 heteroaryl group, or a substituted or unsubstituted fused ring-containing group.

In an implementation, the compound represented by the Chemical Formula 2 may have a characteristic that is appropriate for an electron injection layer or an electron transport layer by including a pyridine, pyrimidine, or 1,3,5-triazine substituent.

In an implementation, the fused ring-containing group may include a moiety represented by one of the following Chemical Formulae "a" to "s".

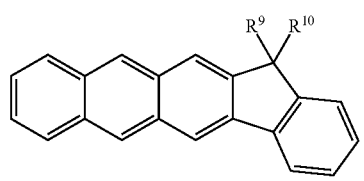

[Chemical Formula a]

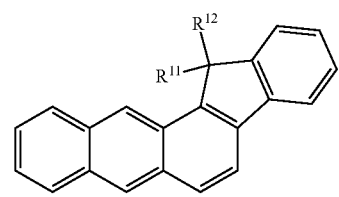

[Chemical Formula b]

-continued
[Chemical Formula c]
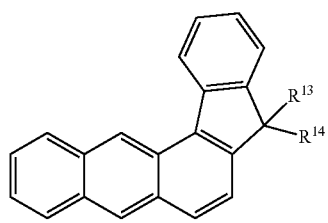
[Chemical Formula d]
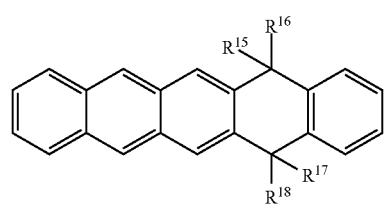
[Chemical Formula e]
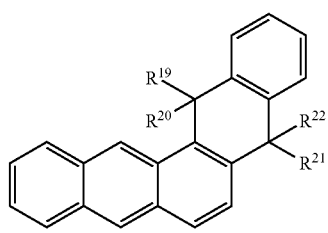
[Chemical Formula f]
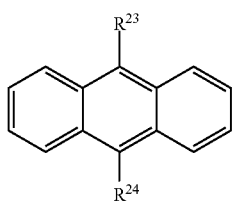
[Chemical Formula g]
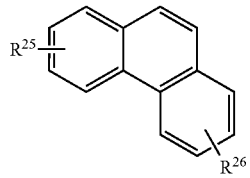
[Chemical Formula h]
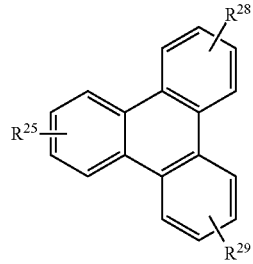
[Chemical Formula i]
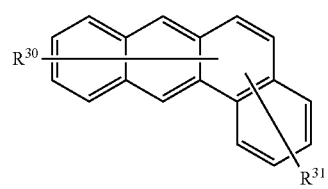
[Chemical Formula j]
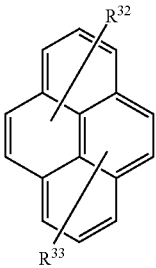
[Chemical Formula k]
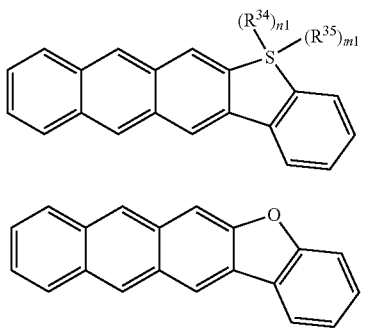
[Chemical Formula l]
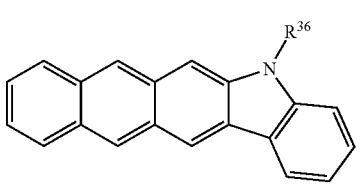
[Chemical Formula m]
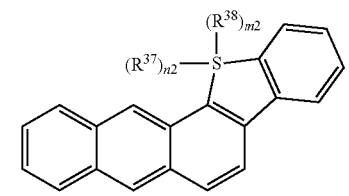
[Chemical Formula n]
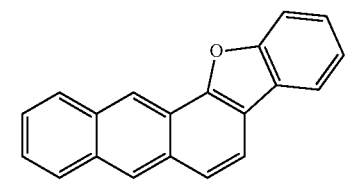
[Chemical Formula o]
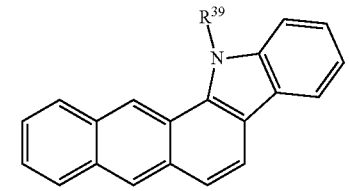
[Chemical Formula p]
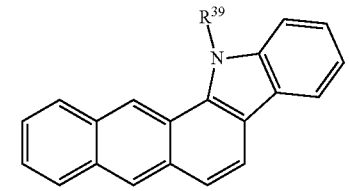

[Chemical Formula q]

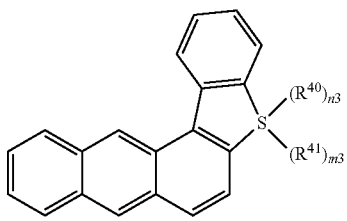

[Chemical Formula r]

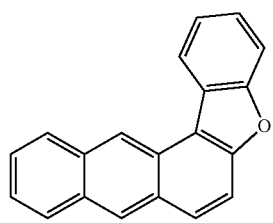

[Chemical Formula s]

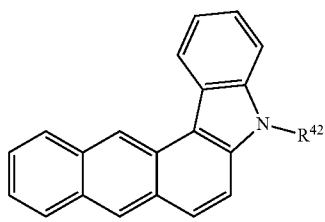

In Chemical Formulae "a" to "s", $R^9$ to $R^{42}$ may each independently be hydrogen, heavy hydrogen, a substituted or unsubstituted C1 to C30 alkyl group, a substituted or unsubstituted C6 to C30 aryl group, or a substituted or unsubstituted C2 to C30 heteroaryl group.

In an implementation, $R^9$ to $R^{42}$ may each independently be the substituted or unsubstituted C1 to C30 alkyl group.

In the Chemical Formulae "a" to "s", n1, n2, n3, m1, m2, and m3 may each independently be 0 or 1. If n1, n2, n3, m1, m2, or m3 is 0, $(R^{34})_{n1}$, $(R^{35})_{m1}$, $(R^{37})_{n2}$, $(R38)_{m2}$, $(R^{40})_{n3}$, or $(R^{41})_{m3}$ may not be present or may be a hydrogen atom.

In an implementation, X may be NR, and R may be a substituted or unsubstituted C6 to C30 aryl group. For example, R may be a phenyl group. In this case, an electron characteristic of the compound may be improved.

In an implementation, all of $R^1$, $R^3$, and $R^4$ may be hydrogen, and $R^2$ may be a substituted or unsubstituted C6 to C50 aryl group. For example, $R^2$ may be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, or a substituted or unsubstituted pyrenyl group. In this case, a hole characteristic and/or an electron characteristic of the compound may be appropriately adjusted.

Detailed examples of the compound according to an exemplary embodiment will now be described. However, it is not limited thereto. The compound represented by Chemical Formula 1 may be a compound represented by one of Chemical Formulae 3 to 51, below.

[Chemical Formulae 3, 4, 5, and 6]

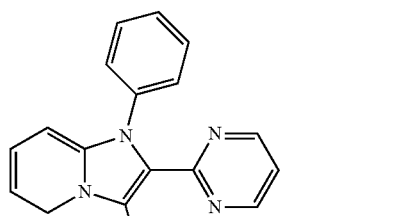

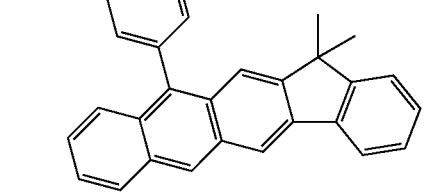

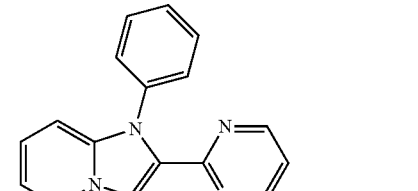

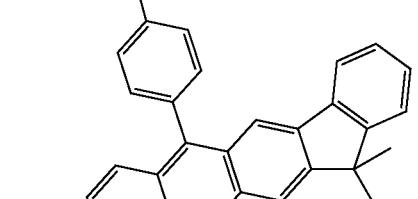

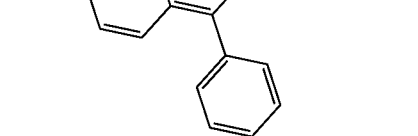

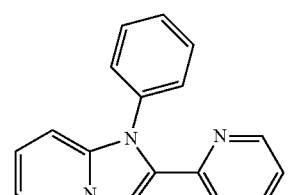

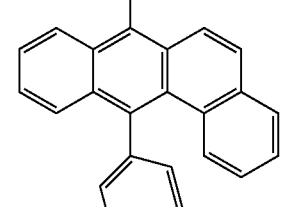

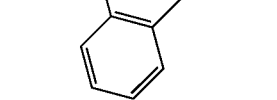

-continued
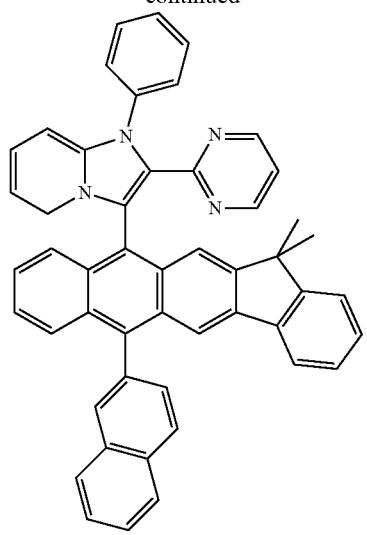
[Chemical Formulae 7, 8, 9 and 10]
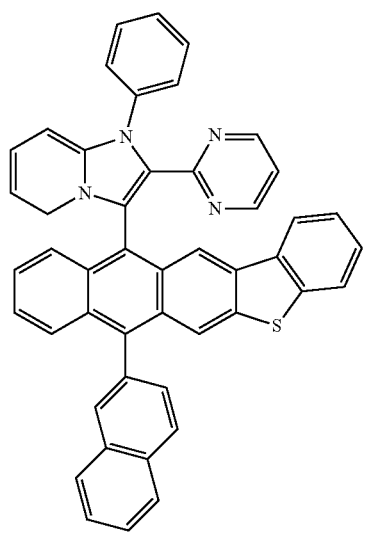
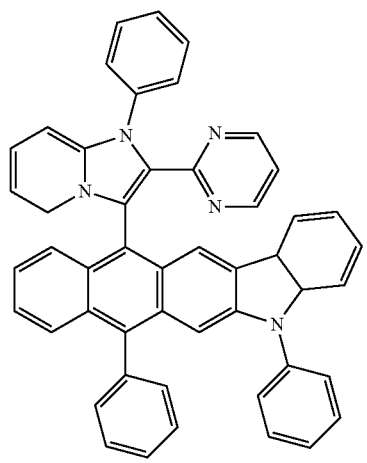
-continued
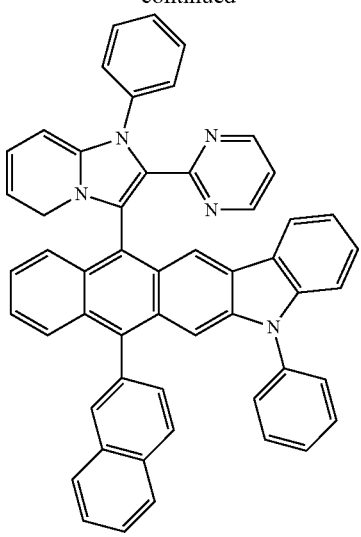
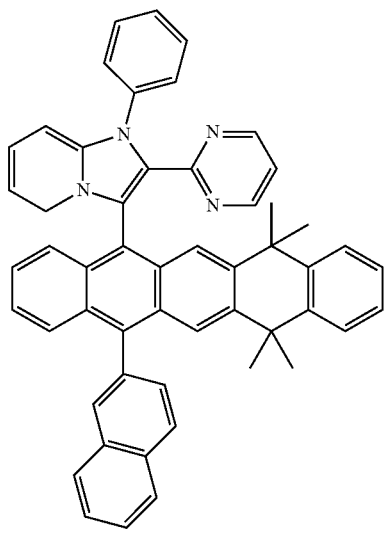
[Chemical Formulae 11, 12, 13, and 14]
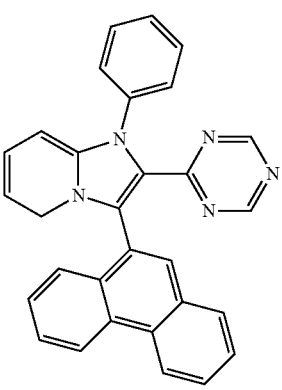

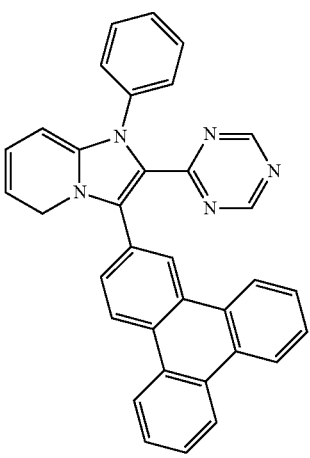
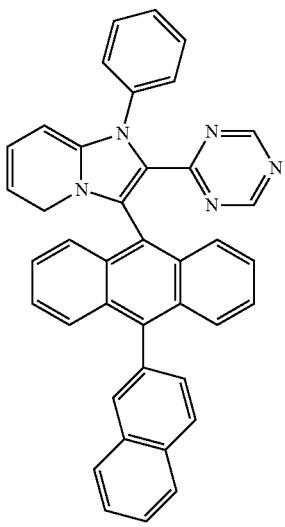
[Chemical Formulae 15, 16, 17, and 18]
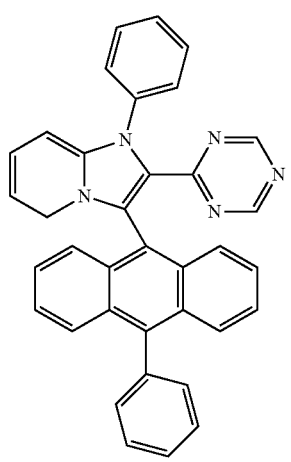
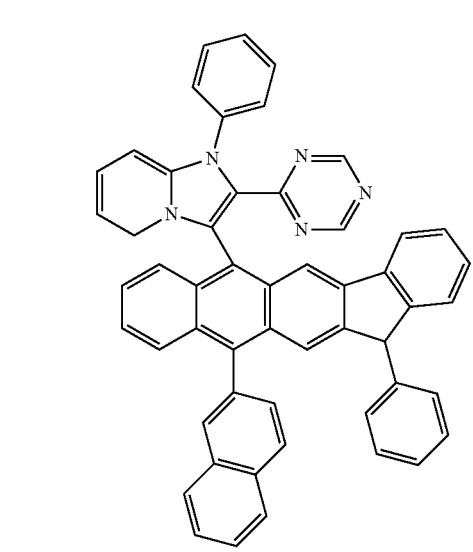
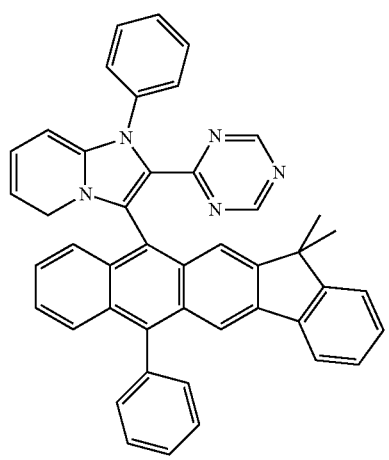
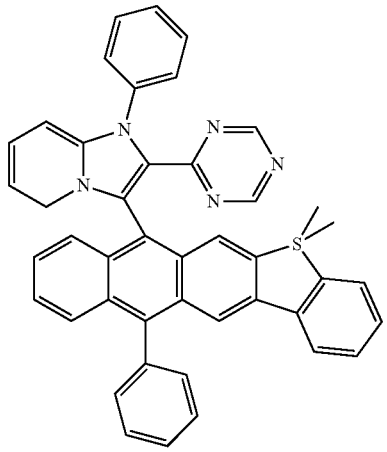

-continued
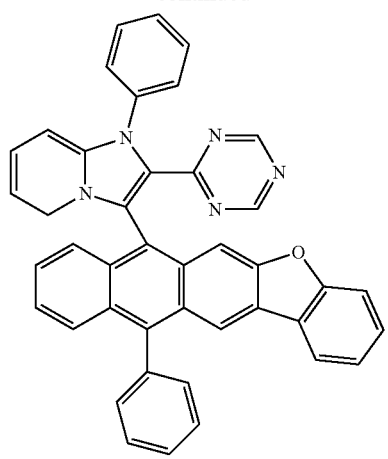
[Chemical Formulae 19, 20, 21, and 22]
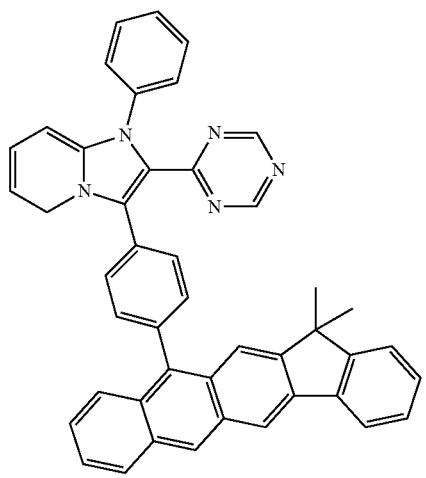
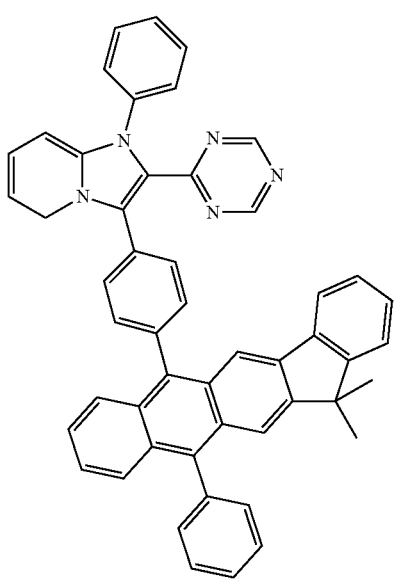
-continued
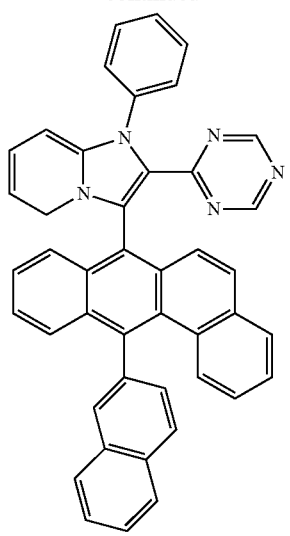
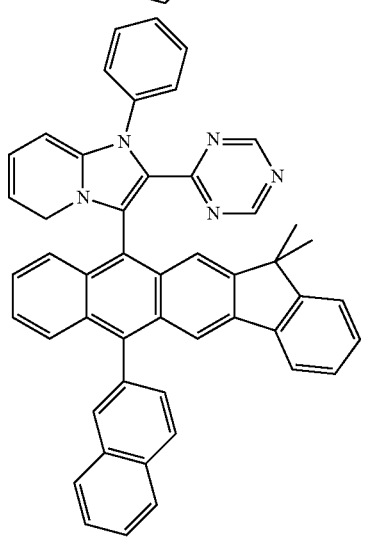
[Chemical Formulae 23, 24, 25, and 26]
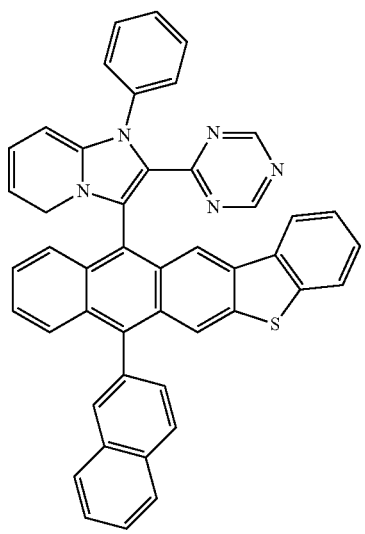

35
-continued
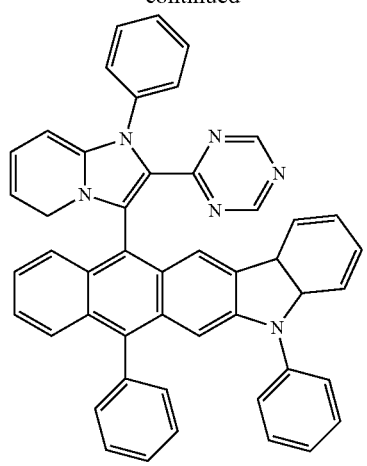
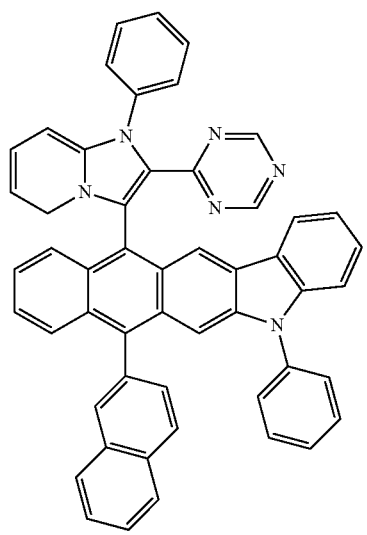
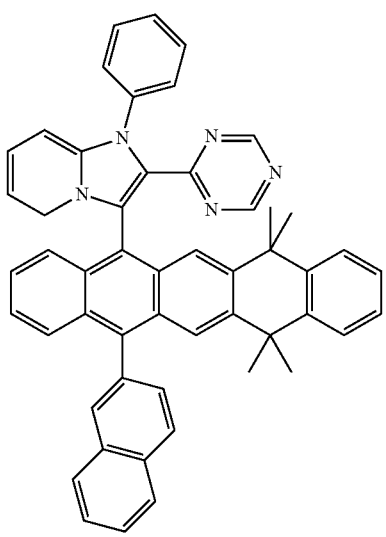
36
-continued
[Chemical Formulae 27, 28, 29, and 30]
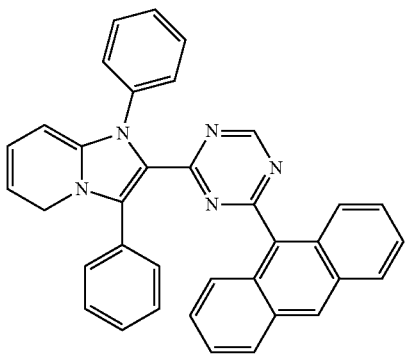
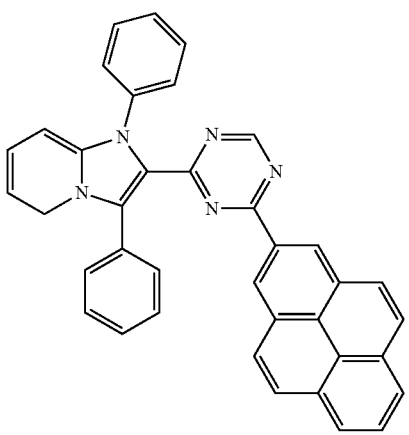
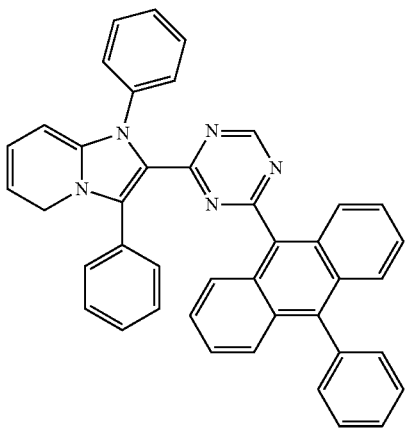

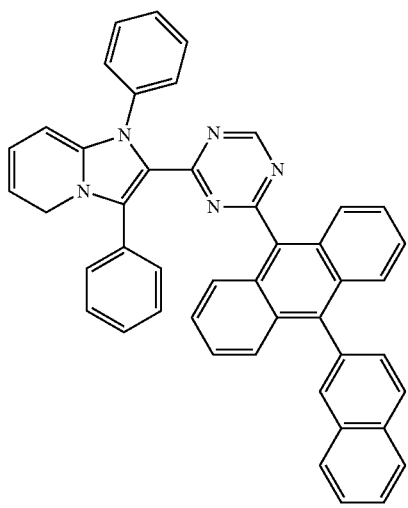
[Chemical Formula 31, 32, and 33]
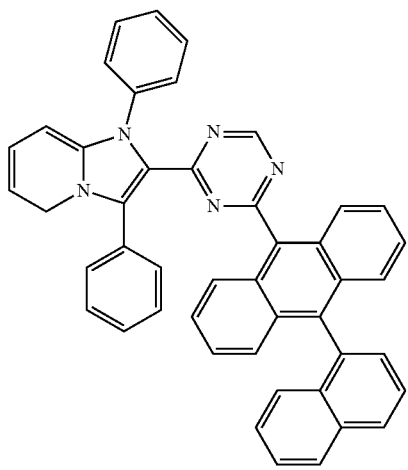
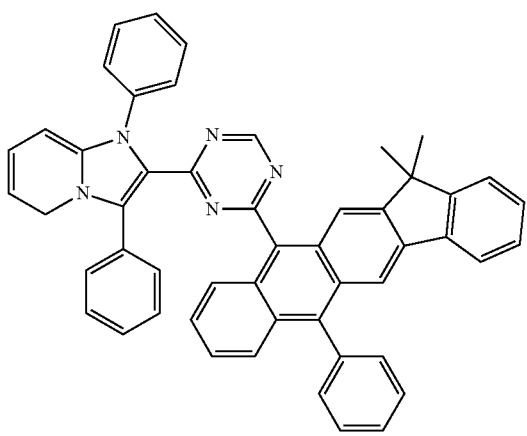
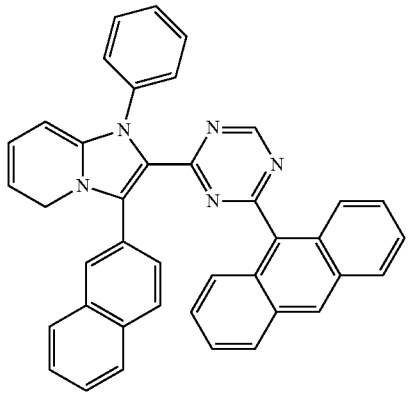
[Chemical Formulae 34, 35, and 36]
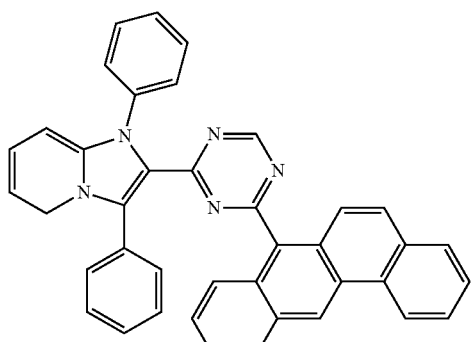
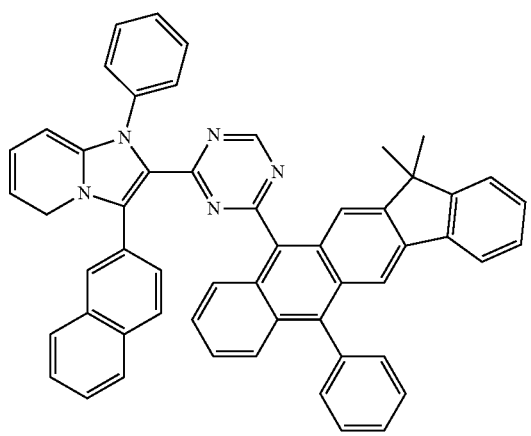
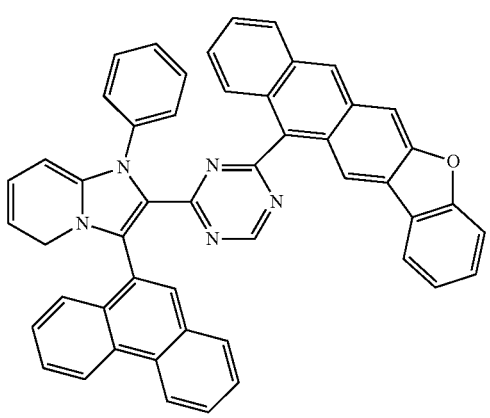

-continued
[Chemical Formulae 37, 38, and 39]
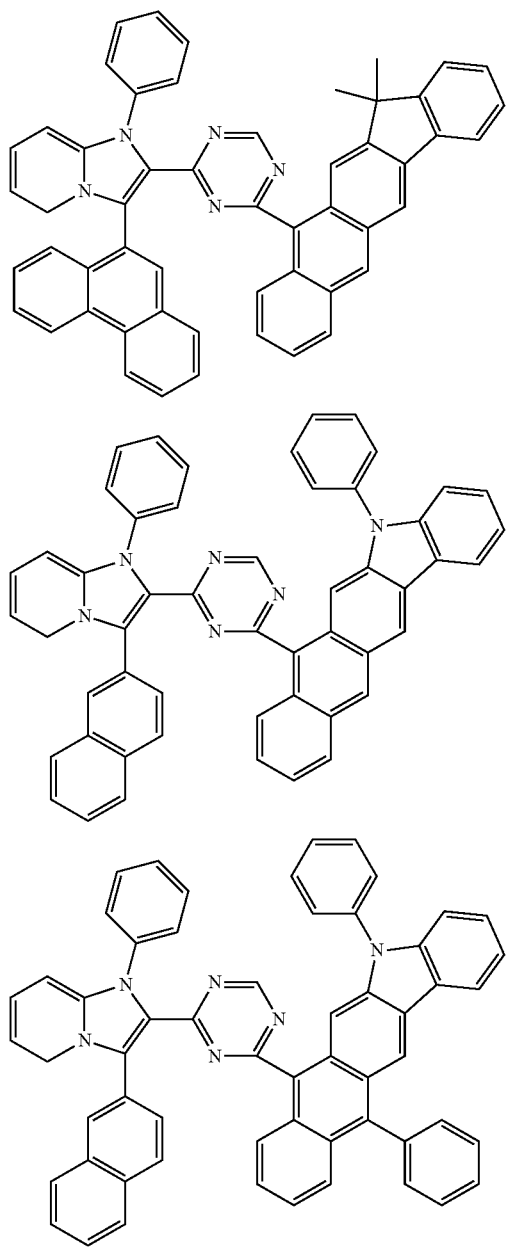
[Chemical Formulae 40, 41, and 42]
-continued
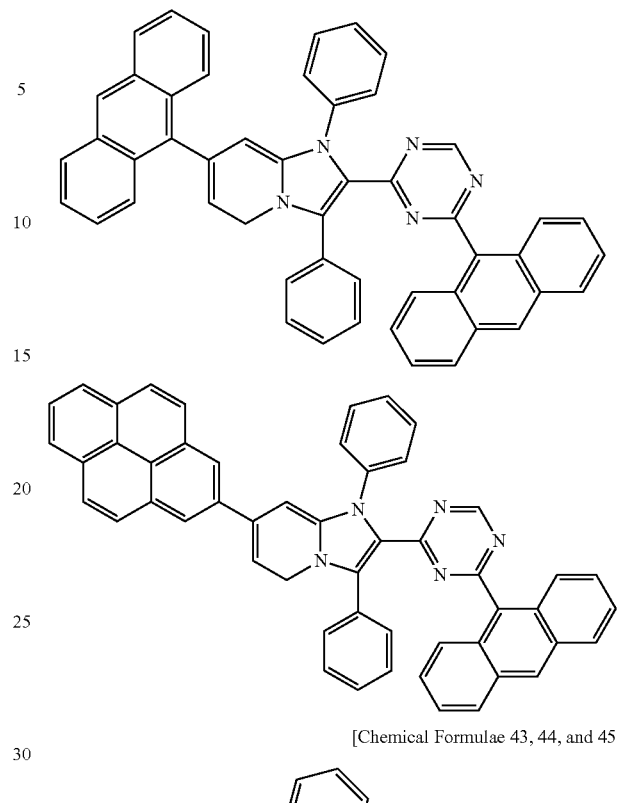
[Chemical Formulae 43, 44, and 45]
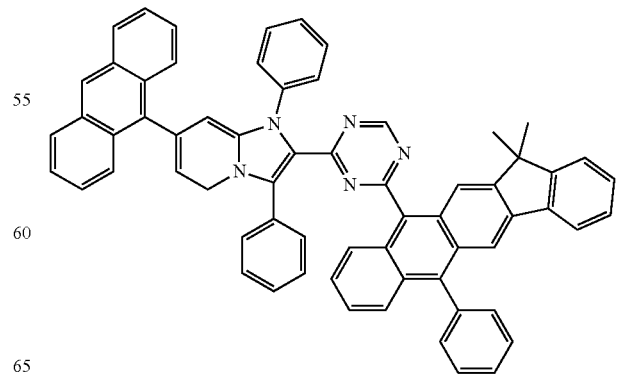

[Chemical Formulae 46, 47, and 48]

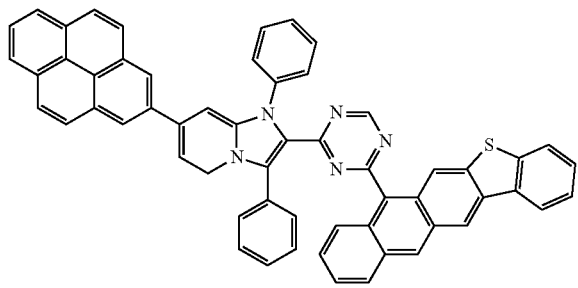

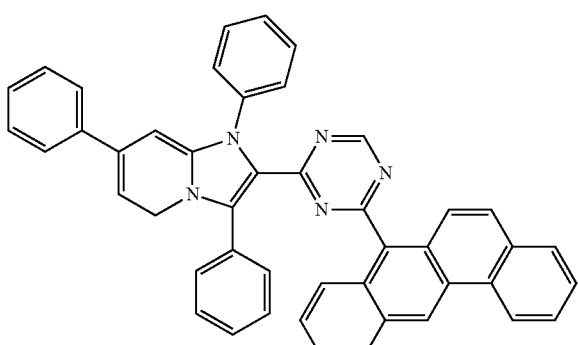

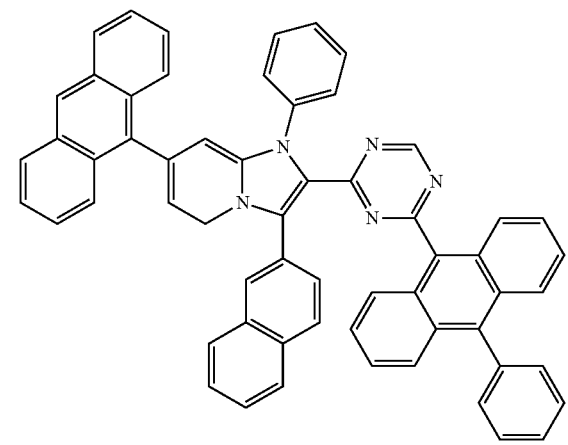

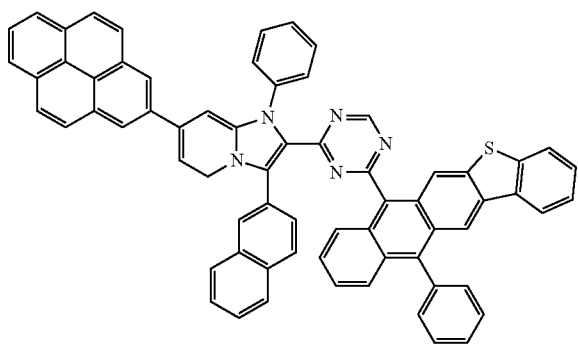

[Chemical Formulae 49, 50, and 51]

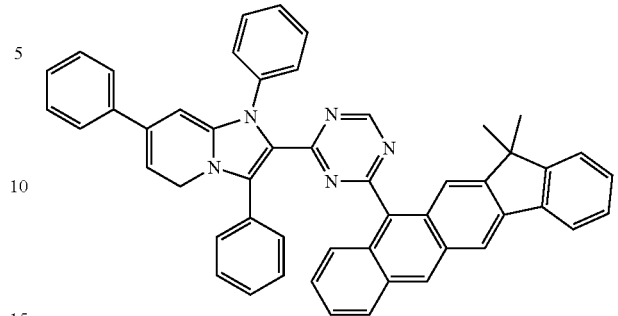

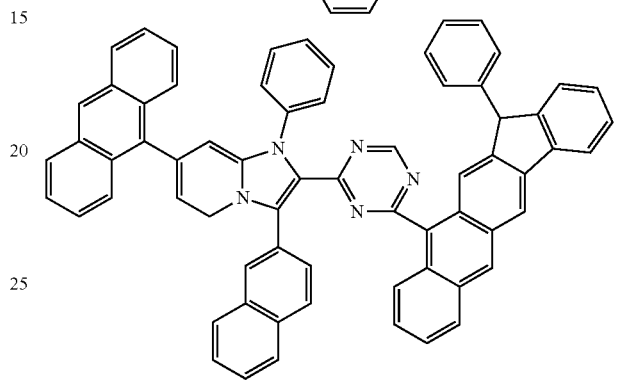

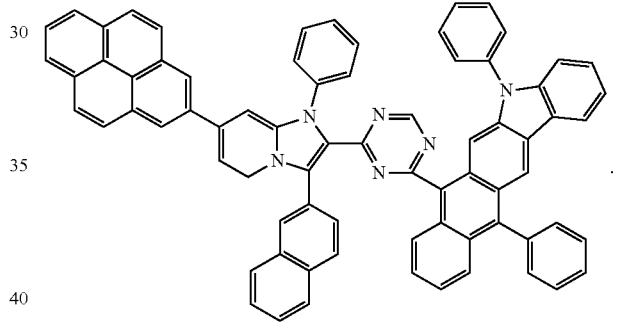

Hereinafter, an organic light emitting diode device including the aforementioned organic compound according to an exemplary embodiment will be described with reference to FIG. 1 to FIG. 3.

Figure 2:
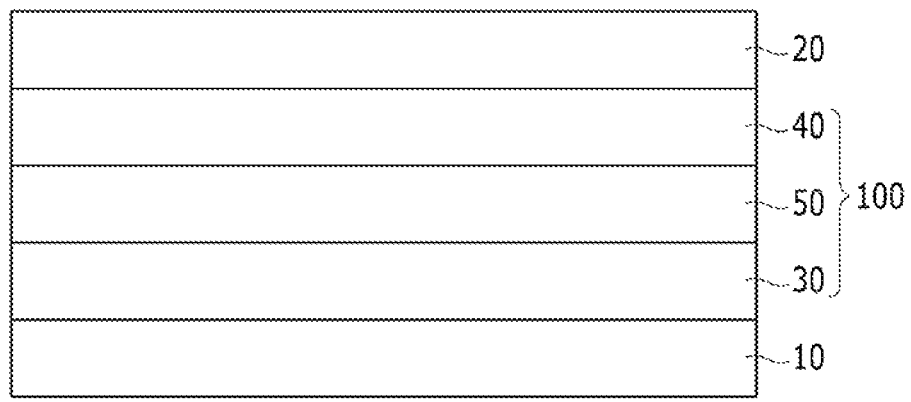
Figure 3:
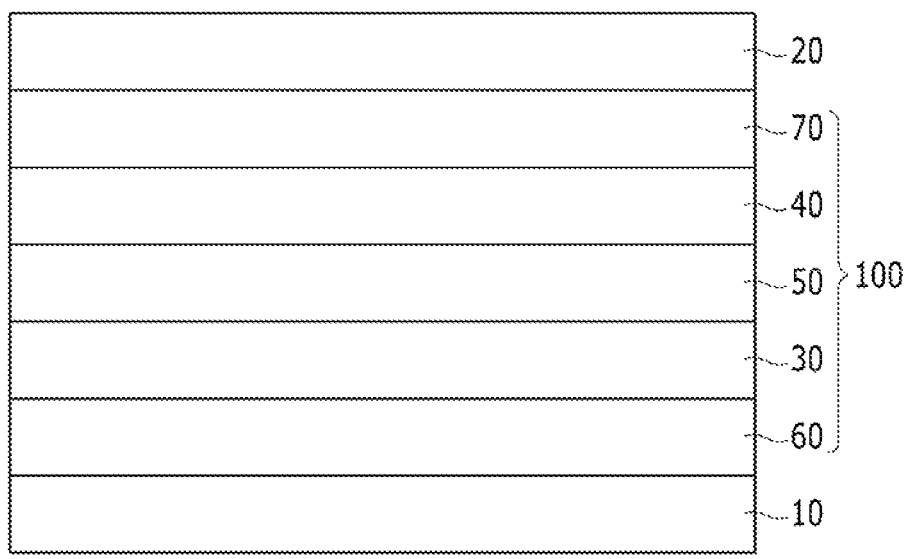

FIG. 1 to FIG. 3 illustrate the structure of an organic light emitting diode device according to an exemplary embodiment.

Referring to FIG. 1, the organic light emitting diode device of the present exemplary embodiment may include an anode 10, a cathode 20 facing the anode 10, and an organic layer 100 between the anode 10 and the cathode 20.

The organic layer 100 may include a compound according to the aforementioned exemplary embodiment, e.g., a compound represented by Chemical Formula 1.

The organic layer 100 may be formed by using various methods such as a vacuum deposition method, a spin coating method, a cast method, an LB method, or the like.

When an organic layer is formed by using the vacuum deposition method, the deposition conditions may vary according to the material that is used to form the organic layer, and the structure and thermal characteristics of the organic layer. For example, the deposition conditions may include a deposition temperature of from about 100° C. to 500° C., a vacuum pressure of about $10^{-8}$ to about $10^{-3}$ torr, and a vacuum rate of from about 0.01 to about 100 Å/sec, without being limited thereto.

When an organic layer is formed by using the spin coating method, the coating conditions may vary according to the material used to form the organic layer, and the structure and thermal characteristics of the organic layer. For example, the coating conditions may include a coating speed of from about 2,000 rpm to about 5,000 rpm and a thermal treatment temperature of from about 80° C. to about 200° C., at which the solvent remaining after coating may be removed, without being limited thereto.

The substrate (not shown) may be disposed at a side of the anode 10 or the cathode 20. The substrate may be made of, e.g., an inorganic material such as glass, an organic material such as polycarbonate (PC), polymethylmethacrylate (PMMA), polyethylene terephthalate (PET), polyamide (PA), polyethersulfone (PES), or a combination thereof, a silicon wafer, or the like.

The anode 10 may be a transparent or non-transparent electrode. The transparent electrode may be made of a conductive oxide, e.g., indium thin oxide (ITO), indium zinc oxide (IZO), tin oxide ($SnO_2$), zinc oxide (ZnO), or a combination thereof, or a metal such as aluminum, silver, or magnesium, having a thin thickness. The non-transparent electrode may be made of, e.g., a metal, e.g., aluminum, silver, or magnesium.

The cathode 20 may contain a substance with a small work function to facilitate electron injection. The substance may include, e.g., a metal such as magnesium, calcium, sodium, potassium, titanium, indium, yttrium, lithium, gadolinium, aluminum, silver, tin, lead, cesium, barium, or an alloy thereof, or a multi-layer structure substance such as LiF/Al, $LiO_2$/Al, LiF/Ca, LiF/Al, or $BaF_2$/Ca. In an implementation, the electrode of a metal such as aluminum or the like may be employed as the cathode.

An organic light emitting diode device according to another embodiment will be described with reference to FIG. 2.

Referring to FIG. 2, similar to the above exemplary embodiment, the organic light emitting diode device of the present embodiment may include an anode 10, a cathode 20 facing the anode 10, and an organic layer 100 between the anode 10 and the cathode 20. The organic layer 100 may include an emission layer 50 between the anode 10 and the cathode 20, a hole transport layer 30 between the anode 10 and the emission layer 50, and an electron transport layer 40 between the cathode 20 and the emission layer 50.

The electron transport layer 40 may include the compound according to the aforementioned embodiment to, e.g., help increase electron mobility.

The electron transport layer 40 may further include a metal-containing material in addition to the compound according to the aforementioned embodiment.

The metal-containing material may include a Li complex. The Li complex may include, e.g., lithium quinolate (LiQ) or a compound represented by the following compound 103.

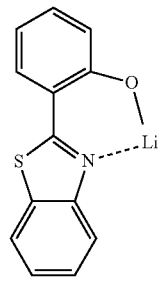

[Compound 103]

The electron transport layer 40 may be formed on the emission layer 50 by using various methods, e.g., a vacuum deposition method, a spin coating method, a casting method, and the like. When the electron transport layer 40 is formed by using the vacuum deposition method or the spin coating method, the conditions may be varied depending on a compound that is employed therefor.

In an implementation, the emission layer 50 may contain a single compound only, or may contain a mixture of the compound and another organic compound. When the emission layer 50 contains the mixture, a larger amount of compounds may serve as fluorescent hosts or phosphorescent hosts, and a smaller amount of compounds may serve as dopants.

An example of a host material may include 9,10-di(naphtalene-2-yl)anthracene (ADN).

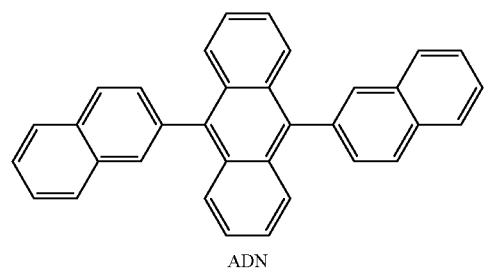

ADN

Examples of a red dopant may include PtOEP, Ir(piq)$_3$, Btp$_2$Ir(acac), and DCJTB.

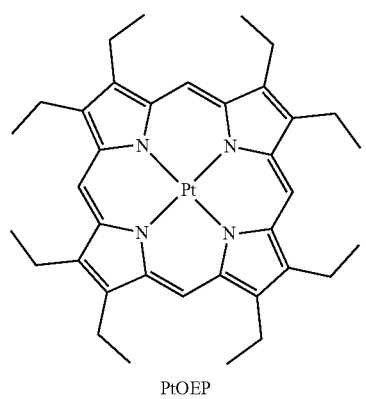

PtOEP

-continued
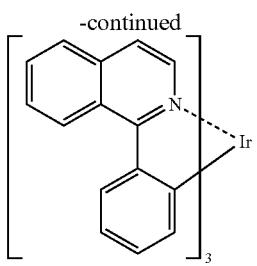
Ir(piq)₃
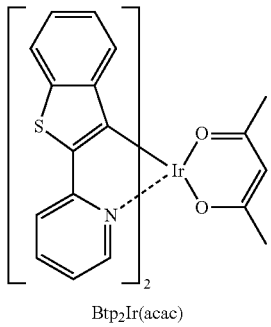
Btp₂Ir(acac)
Examples of a green dopant may include Ir(ppy)₃ (ppy=phenylpyridine), Ir(ppy)₂(acac), Ir(mpyp)₃, and C545T.
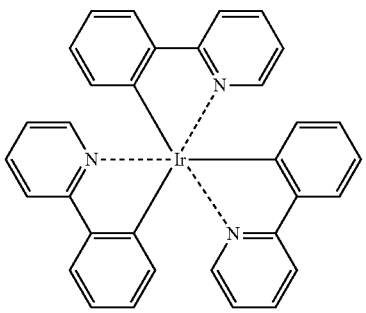
Ir(ppy)₃
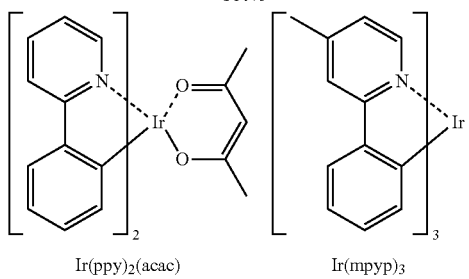
Ir(ppy)₂(acac)   Ir(mpyp)₃
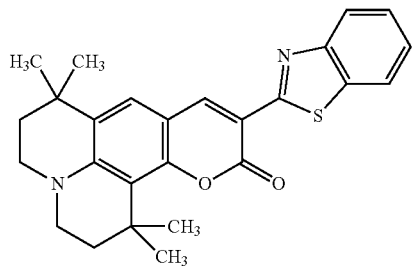
C545T
Examples of a blue dopant may include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-tert-butyl perylene (TBP).
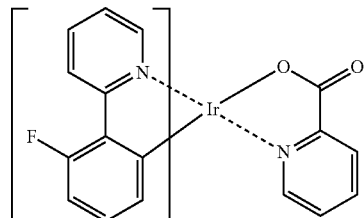
F₂Irpic
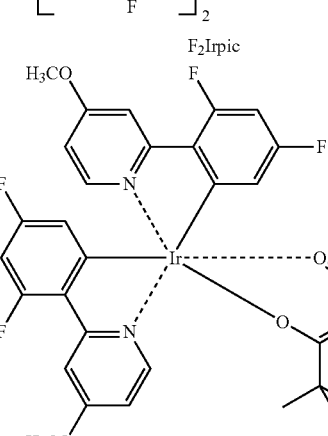
(F₂ppy)₂Ir(tmd)
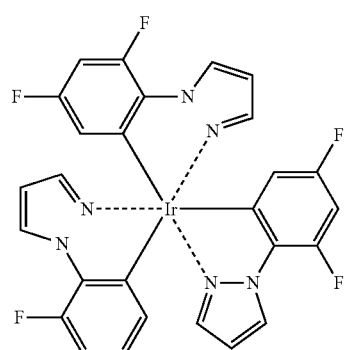
Ir(dfppz)₃
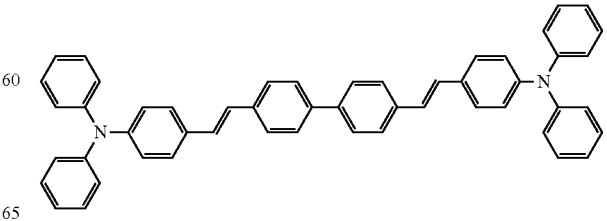
DPAVBi

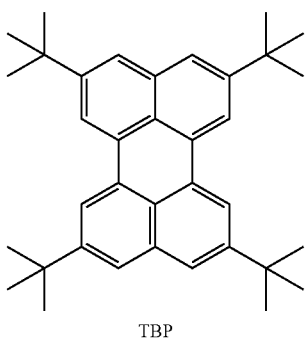

TBP

The dopant may be included in an amount of about 0.1 to about 15 weight %, based on 100 weight % of an emission layer forming material (e.g., a total weight if the host and the dopant is determined as 100 weight %). When the content of the dopant satisfies the range, it is possible to substantially prevent concentration quenching.

The emission layer 50 may emit white light by a combination of the primary colors such as three primary colors of red, green, and blue, and the white light may be emitted by combining the colors of the adjacent subpixels or by combining the colors that are deposited in the vertical direction.

The hole transport layer 30 may help increase hole mobility.

The hole transport layer 30 may include a suitable hole transport material. Examples of the hole transport material may include a carbazole derivative such as N-phenylcarbazole, polyvinylcarbazole, and 4,4',4"-tris(carbazole-9-yl)-triphenylamine, and an amine derivative having an aromatic condensed ring such as NPB and N,N-bis(3-methylphenyl)-N,N'-diphenyl-[1,1-biphenyl]-4,4'-diamine (TPD). In the case of containing TCTA, the hole transport layer 30 may perform not only a hole transport operation but also an operation for preventing diffusion of excitons from the emission layer.

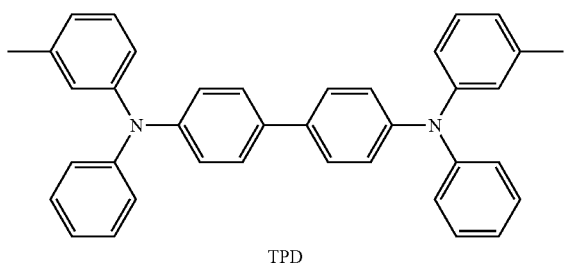

TPD

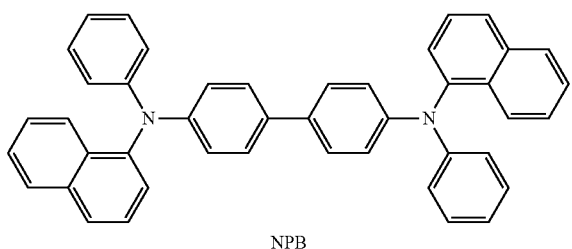

NPB

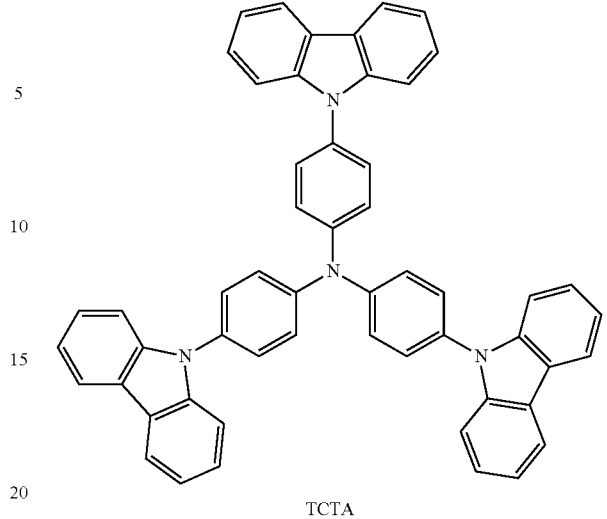

TCTA

The hole transport layer 30 may further contain an auxiliary material to help improve film conductivity and the like.

The auxiliary material may be, e.g., a p-dopant. Examples of the p-dopant may include a quinone derivative such as tetracyanoquinodimethane (TCNQ) and 2,3,5,6-tetrafluoro-tetracyano-1,4-benzoquinonedimethane (F4TCNQ) or the like, a metal oxide such as tungsten oxide and molybdenum oxide, and a cyano group-containing compound such as the compound represented by the following compound 100.

[Compound 100]

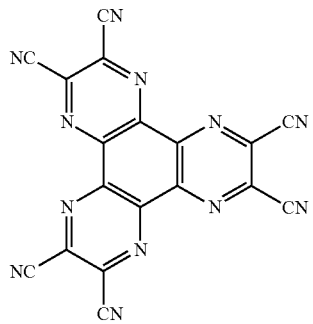

When the hole transport layer 30 further contains the auxiliary material, the auxiliary material may be subject to numerous variations, e.g., non-uniformly distributed or uniformly dispersed over the layers.

Hereinafter, an organic light emitting diode device according to another embodiment will be described with reference to FIG. 3.

Referring to FIG. 3, similar to the above exemplary embodiment, the organic light emitting diode device of the present exemplary embodiment may include an anode 10, a cathode 20 facing the anode 10, an emission layer 50 between the anode 10 and the cathode 20, a hole transport layer 30 between the anode 10 and the emission layer 50, and an electron transport layer 40 between the cathode 20 and the emission layer 50.

The organic light emitting diode device of the present exemplary embodiment may further include a hole injection layer 60 between the anode 10 and the hole transport layer 30, and an electron injection layer 70 between the cathode 20 and the electron transport layer 40.

The hole injection layer 60 may include a suitable hole injection material, e.g., a phthalocyanine compound such as copper phthalocyanine or the like, m-MTDATA (4,4',4''-tris(3-methylphenylphenylamino)triphenylamine), NPB (N,N'-di(1-naphthyl)-N,N'-diphenylbenzidine), TDATA, 2T-NATA, Pani/DBSA (polyaniline/dodecylbenzene sulfonic acid), PEDOT/PSS (poly(3,4-ethylenedioxythiophene)/poly(4-styrenesulfonate)), Pani/CSA (polyaniline/camphor sulfonic acid), or PANI/PSS ((polyaniline)/poly(4-styrenesulfonate)).

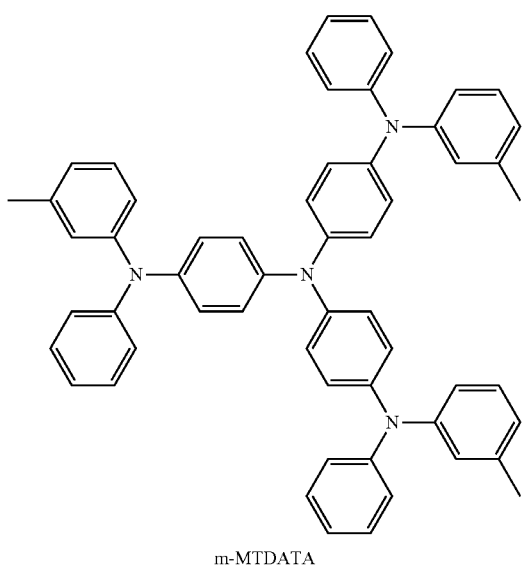

m-MTDATA

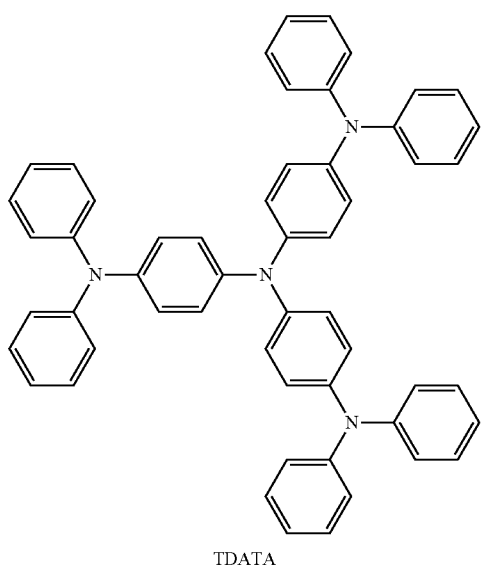

TDATA

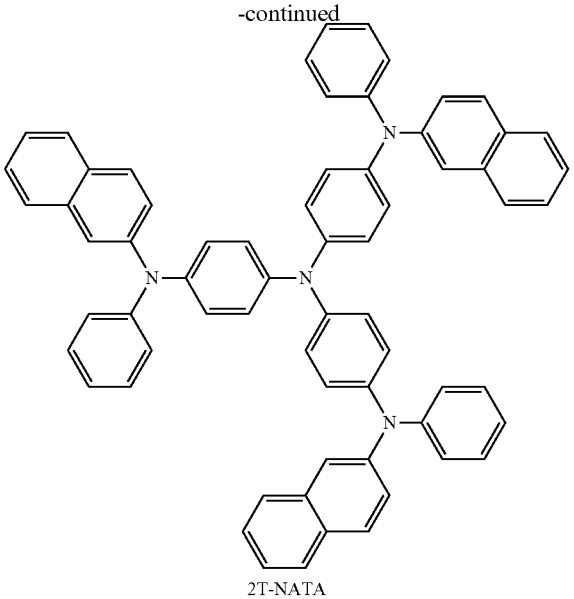

2T-NATA

The hole injection layer 60 may further contain the aforementioned auxiliary material to help improve film conductivity and the like.

When the hole injection layer 60 further contains the auxiliary material, the auxiliary material may be subject to numerous variations, e.g., non-uniformly distributed or uniformly dispersed over the layers.

The hole injection layer 60 may be formed at an upper portion of the anode 10 by using various methods such as a vacuum deposition method, a spin coating method, a casting method, an LB method, or the like.

When the hole injection layer 60 is formed by using the vacuum deposition method, the deposition conditions may be varied depending on a compound employed as the material of the HIL, a desired structure of the HIL, a thermal characteristic, or the like. In an implementation, adequate selections may be made in a vacuum deposition temperature ranging from 100 to 500° C., a vacuum level ranging from $10^{-8}$ to $10^{-3}$ torr, and a vacuum deposition rate ranging 0.01 to 100 Å/sec.

When the hole injection layer 60 is formed by using the spin coating method, the coating conditions may be varied depending on a compound employed as the material of the HIL, a desired structure of the HIL, a thermal characteristic, or the like. In an implementation, adequate selections may be made in a coating rate ranging from about 2,000 rpm to 5,000 rpm, and a heat treatment temperature for solvent removal after coating ranging from about 80 to 200° C.

When the emission layer 50 contains a phosphorescent dopant, a hole blocking layer (not shown) may be formed at an upper portion of the emission layer 50 to help prevent the diffusion of triplet excitons or holes into the electron transport layer. In this case, a hole blocking material employed herein may include a suitable hole blocking material. Examples of the hole blocking material may include an oxadiazole derivative, a triazole derivative, a phenanthroline derivative, Balq, BCP, and the like.

The electron injection layer 70 may be stacked at an upper portion of the electron transport layer 40 to serve as a material for facilitating the injection of electrons from a cathode.

As for the electron injection layer 70, a suitable material may be employed as an EIL forming material, such as LiF, NaCl, CsF, Li$_2$O, BaO, or the like. The vacuum deposition conditions and the coating conditions of the electron injection layer 70 may be varied depending on the compound that is employed. In an implementation, selections may be made in a condition range that is substantially the same as the condition range when the hole injection layer 60 60 is formed.

The organic light emitting diode device according to the present exemplary embodiment may have a structure of anode/hole injection layer/emission layer/cathode, anode/hole injection layer/hole transport layer/emission layer/electron transport layer/cathode, or anode/hole injection layer/hole transport layer/emission layer/electron transport layer/electron injection layer/cathode. In an implementation, the organic light emitting diode device may have a structure of anode functional layer having both a hole injecting function and a hole transport function/emission layer/electron transport layer/cathode, or anode/functional layer having both a hole injecting function and a hole transport function/emission layer/electron transport layer/electron injection layer/cathode. In an implementation, the organic light emitting diode device may have a structure of anode/hole transport layer/emission layer/functional layer having both a hole injecting function and a hole transport function/cathode, anode/hole injection layer/emission layer/layer having both a hole injecting function and a hole transport function/cathode, or anode/hole injection layer/hole transport layer/emission layer/functional layer having both a hole injecting function and a hole transport function/cathode.

The organic light emitting diode device may be electrically connected to, e.g., a thin film transistor. In this case, the thin film transistor may be disposed between a substrate and an electrode.

Further, a first layer of the organic light emitting diode device in accordance with an exemplary embodiment may be formed by using the vacuum deposition method using an organic compound of an exemplary embodiment or a wet processing method of coating an organic compound of an exemplary embodiment.

According to an exemplary embodiment, a display device including the organic light emitting diode device according to the aforementioned exemplary embodiment may be provided.

Hereinafter, the embodiments will be described in more detail by using synthesis examples and test examples. The following test examples are merely described for the purpose of explanation, without limiting the scope of the embodiments.

The following Examples and Comparative Example are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS EXAMPLES

Synthesis Example 1

Synthesis of Chemical Formula 5

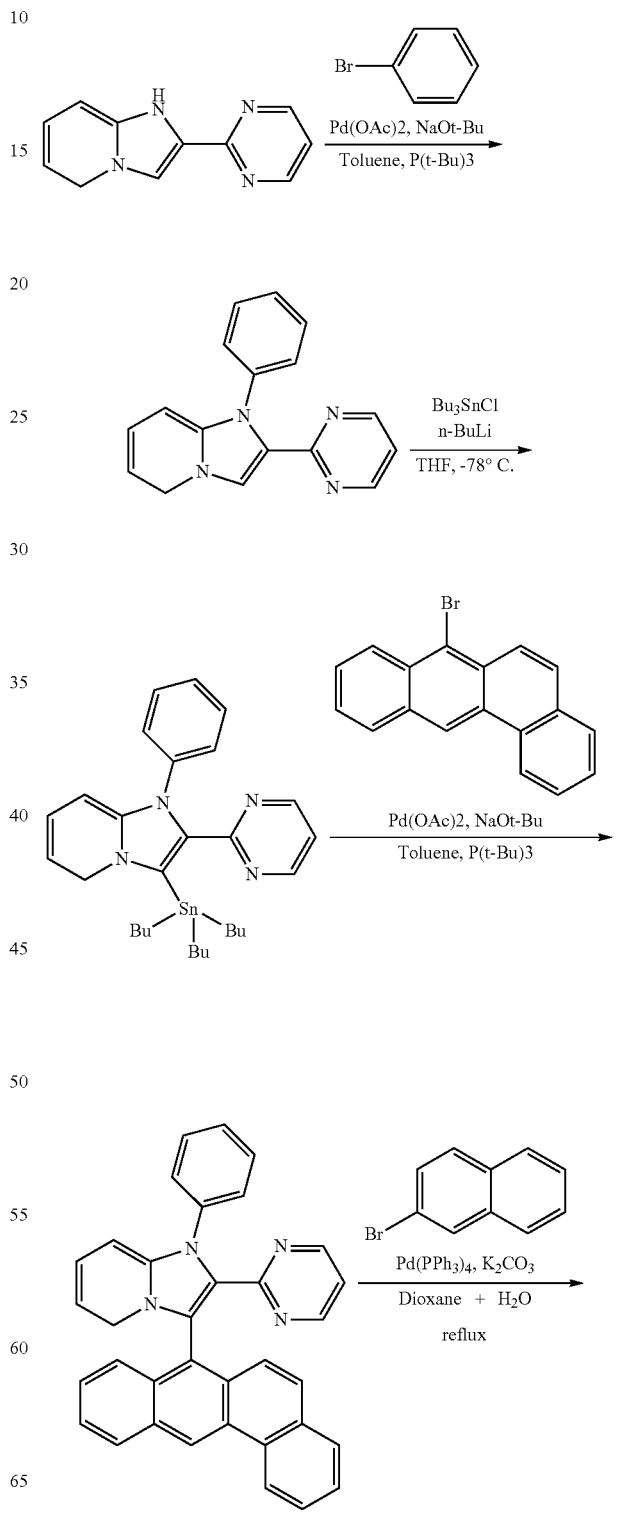

Synthesis Example 2

Synthesis of Chemical Formula 11

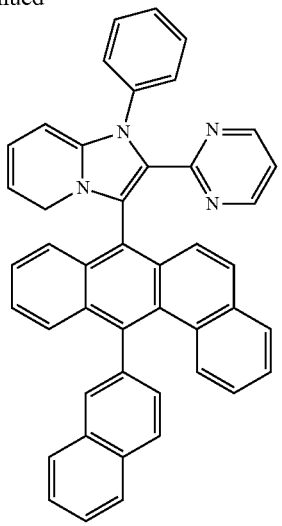

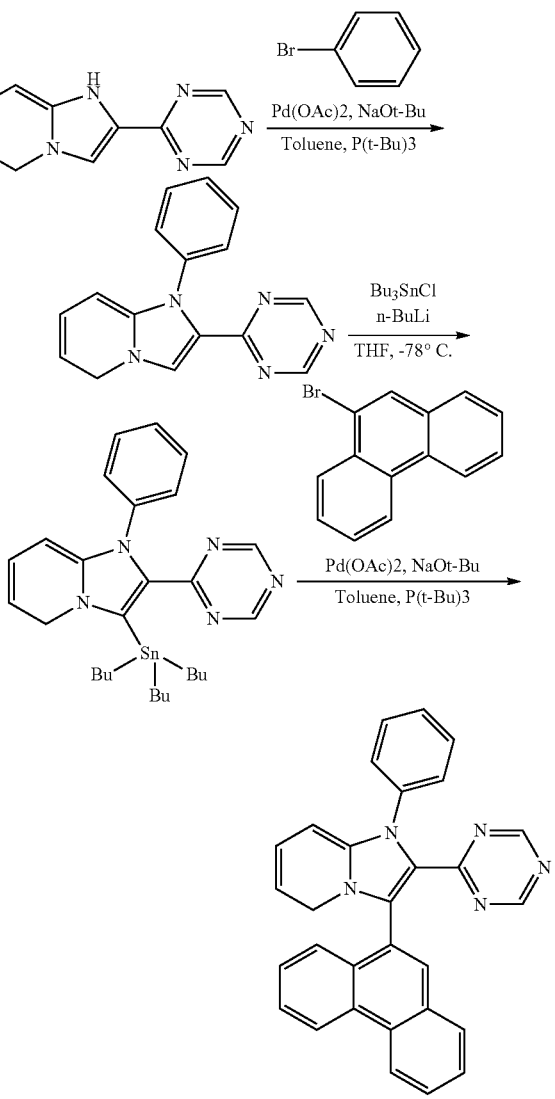

2-(pyrimidin-2-yl)-1,5-dihydroimidazo[1,2-a]pyridine at 7 g (31.32 mmol), bromobenzene at 5.5 g (35.03 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then stirred at ambient (room) temperature for 60 minutes. 1-phenyl-2-(pyrimidin-2-yl)-1,5-dihydroimidazo[1,2-a]pyridine was obtained after the reaction and filtering. 1-phenyl-2-(pyrimidin-2-yl)-1,5-dihydroimidazo[1,2-a]pyridine at 6.92 g (25.23 mmol), BuSnCl at 8.28 g (25.43 mmol), and n-BuLi at 12.81 mg (0.20 mmol) were dissolved in 50 ml of THF, and then stirred at a temperature of −78° C. for 10 minutes. Thereafter, the temperature was increased to ambient temperature. 7-bromotetraphene at 7.13 g (23.2 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then refluxed and stirred at a temperature of 50° C. for 12 hours. The resultant was filtered, and then Pd(PPh$_3$)$_4$ at 23.1 mg (0.02 mmol) and K$_2$CO$_3$ at 3.18 g (23.0 mmol) were added thereinto. The resultant was refluxed and stirred in a solution of 25 ml of dioxane mixed with 25 ml of distilled water at a temperature of 160° C. for 48 hours.

After the reaction was completed, 20 ml of cold distilled water was added thereinto. Then, extraction using ethyl acetate was performed. After a drying operation using magnesium sulfate and filtering, the solvent was evaporated.

Then, 13.02 g of the compound (20.77 mmol, yield 64.3%) represented by Chemical Formula 5 was obtained through column chromatography.

$^1$H NMR (300 MHz, DMSO), d (ppm): 8.98 (1H, d), 8.80 (2H, d), 8.20-7.99 (5H, m), 7.90-7.88 (2H, d), 7.68-7.32 (12H, m), 7.20 (1H, d), 6.58 (2H, d), 6.17 (1H, d), 5.60 (1H, t), 4.73 (1H, s), 3.80 (1H, d)

m/z: 626.25

2-(1,3,5-triazin-2-yl)-1,5-dihydroimidazo[1,2-a]pyridine at 7 g (35.14 mmol), bromobenzene at 6 g (38.21 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then stirred at ambient temperature for 60 minutes. 1-phenyl-2-(1,3,5-triazin-2-yl)-1,5-dihydroimidazo[1,2-a]pyridine was obtained after a the reaction and filtering. 1-phenyl-2-(1,3,5-triazin-2-yl)-1,5-dihydroimidazo[1,2-a]pyridine at 6.95 g (25.23 mmol), BuSnCl at 8.28 g (25.43 mmol), and n-BuLi at 12.81 mg (0.20 mmol) were dissolved in 50 ml of THF, and then stirred at a temperature of −78° C. for 10 minutes. Thereafter, the temperature was increased to ambient temperature. 9-bromophenanthrene at 4.7 g (22.7 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then refluxed and stirred at a temperature of 50° C. for 12 hours. The resultant was filtered, and then 23.1 mg (0.02 mmol) of Pd(PPh$_3$)$_4$ and 3.18 g (23.0 mmol) of K$_2$CO$_3$ were added thereinto. This was refluxed and stirred in a solution of 25 ml of dioxane mixed with 25 ml of distilled water at a temperature of 160° C. for 48 hours.

After the reaction was completed, 20 ml of cold distilled water was added thereinto. Then, extraction using ethyl acetate was performed. After a drying operation using magnesium sulfate and filtering, the solvent was evaporated.

Then, 8.63 g of the compound (19.12 mmol, yield 61.4%) represented by Chemical Formula 11 was obtained through column chromatography.

$^1$H NMR (300 MHz, DMSO), d (ppm): 9.63 (2H, s), 8.98 (1H, d), 8.84 (1H, d), 8.11 (1H, d), 7.90 (1H, d), 7.75-7.62 (5H, m), 7.32 (2H, t), 7.20 (1H, t), 6.58 (2H, d), 6.17 (1H, d), 5.60 (1H, t), 4.73 (1H, s), 3.80 (1H, d)

m/z: 452.18

Synthesis Example 3

Synthesis of Chemical Formula 16

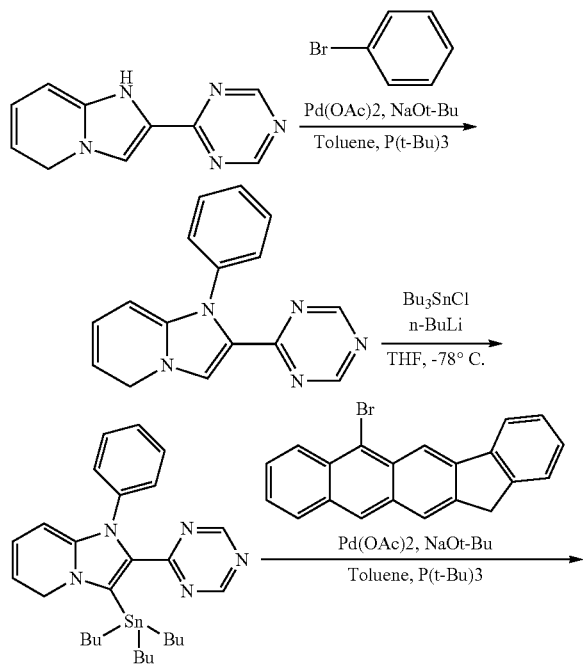

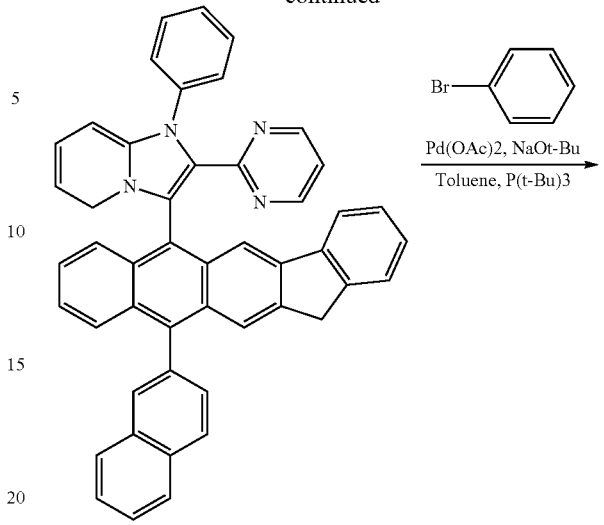

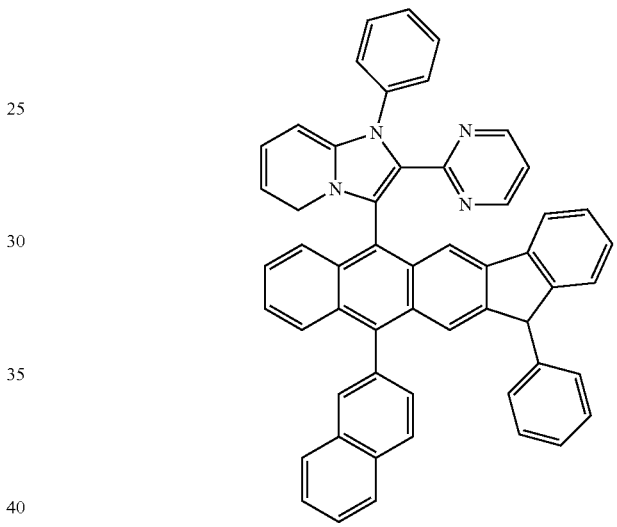

2-(1,3,5-triazin-2-yl)-1,5-dihydroimidazo[1,2-a]pyridine at 7 g (35.14 mmol), bromobenzene at 6 g (38.21 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then stirred at ambient temperature for 60 minutes. 1-phenyl-2-(1,3,5-triazin-2-yl)-1,5-dihydroimidazo[1,2-a]pyridine was obtained after the reaction and filtering. 1-phenyl-2-(1,3,5-triazin-2-yl)-1,5-dihydroimidazo[1,2-a]pyridine at 6.95 g (25.23 mmol), BuSnCl at 8.28 g (25.43 mmol), and n-BuLi at 12.81 mg (0.20 mmol) were dissolved in 50 ml of THF, and then stirred at a temperature of −78° C. for 10 minutes. Thereafter, the temperature was increased to ambient temperature. 6-bromo-13H-indeno[1,2-b]anthracene at 8.80 g (25.5 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then refluxed and stirred at a temperature of 50° C. for 12 hours. The resultant was filtered, and then 2-bromonaphthalene at 4.76 g (23.01 mmol), Pd(PPh$_3$)$_4$ at 23.1 mg (0.02 mmol), and K$_2$CO$_3$ at 3.18 g (23.0 mmol) were added thereinto. This were refluxed and stirred in a solution of 25 ml of dioxane mixed with 25 ml of distilled water at a temperature of 160° C. for 48 hours, thereby obtaining 3-11-(naphthalen-2-yl)-13H-indeno[1,2-b]anthracen-6-yl)-1-phenyl-2-(pyrimidin-2-yl)-1,5-dihydroimidazo[1,2-a]pyridine.

3-(11-(naphthalen-2-yl)-13H-indeno[1,2-b]anthracen-6-yl)-1-phenyl-2-(pyrimidin-2-yl)-1,5-dihydroimidazo[1,2-a]pyridine at 14 g (21.0 mmol), bromobenzene at 3.6 g (23.0 mmol), Pd(OAc)₂ at 13.5 mg (0.06 mmol), NaOt-Bu at 5.76 mg (0.06 mmol), and P(t-Bu)₃ at 11.52 mg (0.057 mmol) were dissolved in 10 ml of toluene, and then stirred at ambient temperature for 60 minutes.

After the reaction was completed, 20 ml of cold distilled water was added thereinto. Then, extraction using ethyl acetate was performed. After a drying operation using magnesium sulfate and filtering, the solvent was evaporated. Then, 813.42 g of the compound (18.11 mmol, yield 47.4%) represented by Chemical Formula 16 was obtained through column chromatography.

¹H NMR (300 MHz, DMSO), d (ppm): 8.80 (2H, d), 8.24-8.18 (2H, d), 8.09-7.92 (6H, m), 7.74 (1H, d), 7.63-7.52 (5H, m), 7.40-7.14 (12H, m), 6.58 (2H, d), 6.17 (1H, d), 5.60 (1H, t), 5.15 (1H, s), 4.73 (1H, s), 3.80 (1H, d)

m/z: 664.26

Synthesis Example 4

Synthesis of Chemical Formula 22

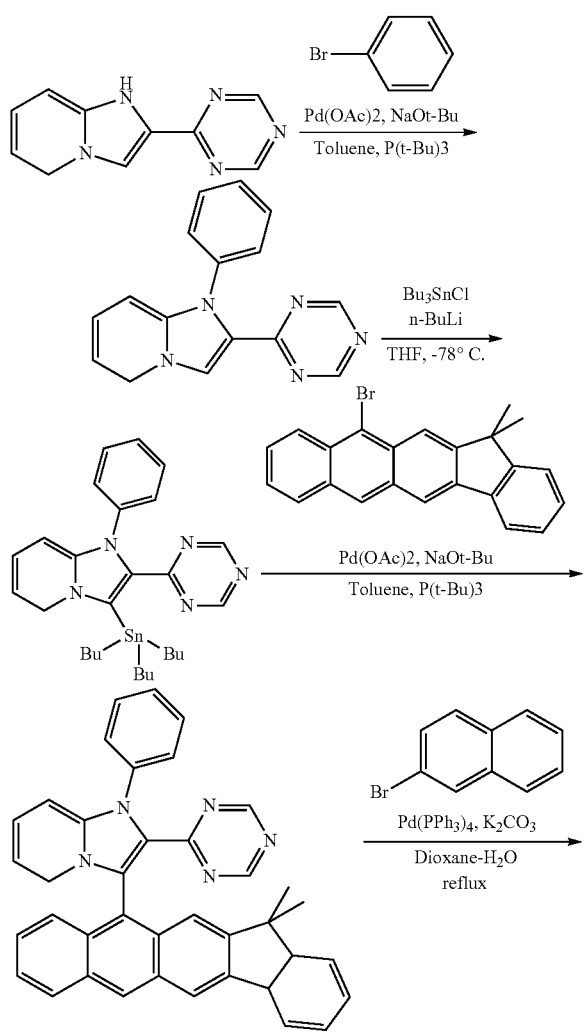

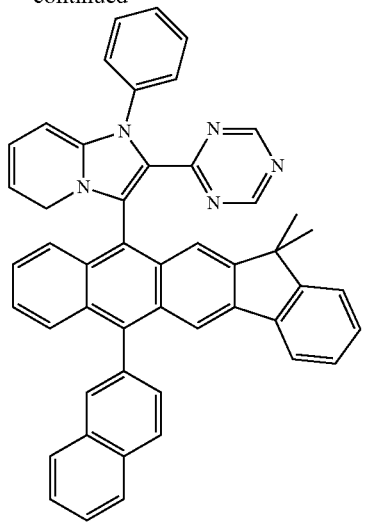

2-(1,3,5-triazin-2-yl)-1,5-dihydroimidazo[1,2-a]pyridine at 7 g (35.14 mmol), bromobenzene at 6 g (38.21 mmol), Pd(OAc)₂ at 44.9 mg (0.2 mmol), NaOt-Bu at 19.22 mg (0.20 mmol), and P(t-Bu)₃ at 38.37 mg (0.19 mmol) were dissolved in 20 ml of toluene, and then stirred at ambient temperature for 60 minutes. 1-phenyl-2-(1,3,5-triazin-2-yl)-1,5-dihydroimidazo[1,2-a]pyridine was obtained after a thus-generated reaction and filtering. 1-phenyl-2-(1,3,5-triazin-2-yl)-1,5-dihydroimidazo[1,2-a]pyridine at 6.95 g (25.23 mmol), BuSnCl at 8.28 g (25.43 mmol), and n-BuLi at 12.81 mg (0.20 mmol) were dissolved in 50 ml of THF, and then stirred at a temperature of −78° C. for 10 minutes. Thereafter, the temperature was increased to ambient temperature. 11-bromo-13,13-dimethyl-13H-indeno[1,2-b]anthracene at 8.14 g (21.8 mmol), Pd(OAc)₂ at 44.9 mg (0.2 mmol), NaOt-Bu at 19.22 mg (0.20 mmol), and P(t-Bu)₃ at 38.37 mg (0.19 mmol) were dissolved in 20 ml of toluene, and then refluxed and stirred at a temperature of 50° C. for 12 hours. The resultant was filtered, and then 2-bromonaphthalene at 4.76 g (23.01 mmol), Pd(PPh₃)₄ at 23.1 mg (0.02 mmol), and K₂CO₃ at 3.18 g (23.0 mmol) were added thereinto. This was refluxed and stirred in a solution of 25 ml of dioxane mixed with 25 ml of distilled water at a temperature of 160° C. for 48 hours.

After the reaction was completed, 30 ml of cold distilled water was added thereinto.

Then, extraction using ethyl acetate was performed. After a drying operation using magnesium sulfate and filtering, the solvent was evaporated. Then, 9.89 g of the compound (14.26 mmol, yield 37.31%) represented by Chemical Formula 22 was obtained through column chromatography.

¹H NMR (300 MHz, DMSO), d (ppm): 9.63 (2H, s), 8.24-8.18 (2H, d), 8.10-7.93 (6H, m), 7.74 (1H, d), 7.63-7.55 (4H, m), 7.40-7.32 (6H, m), 7.20 (1H, d), 6.58 (2H, d), 6.17 (1H, d), 5.60 (1H, t), 4.73 (1H, s), 3.80 (1H, d), 1.75 (2H, s)

m/z: 693.29

Synthesis Example 5

Synthesis of Chemical Formula 29

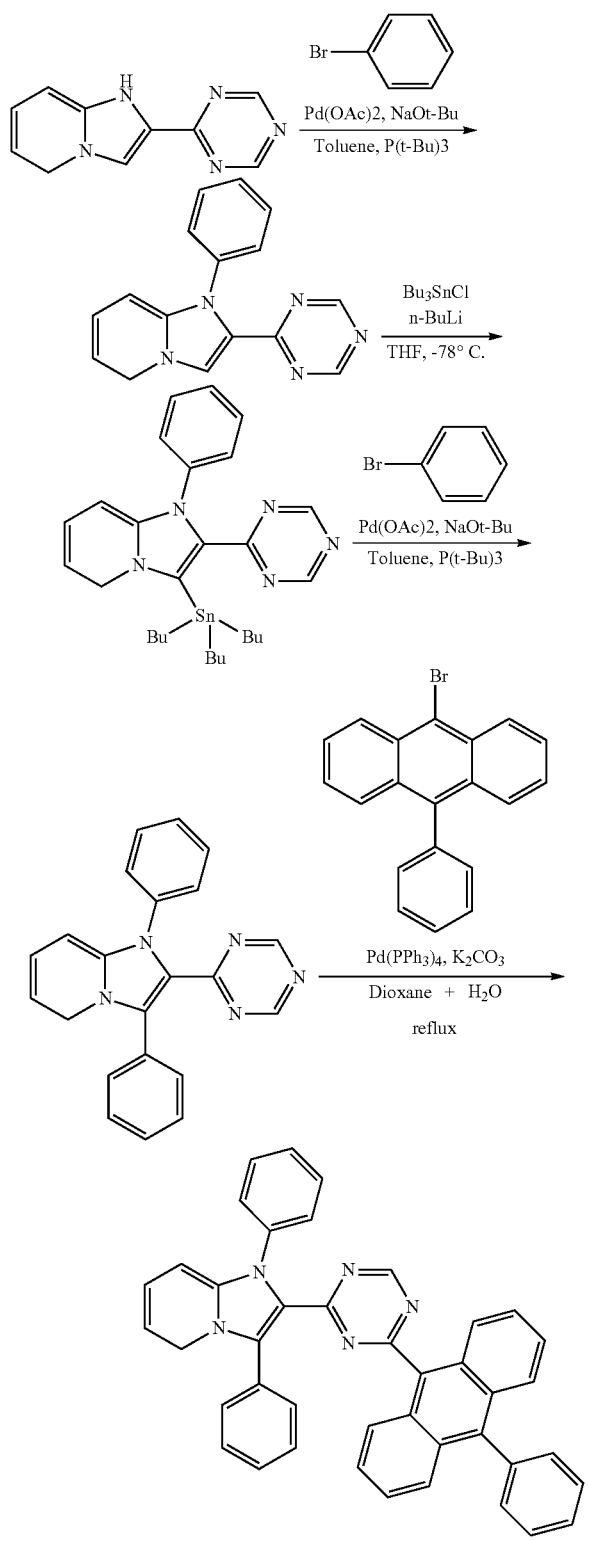

2-(1,3,5-triazin-2-yl)-1,5-dihydroimidazo[1,2-a]pyridine at 7 g (35.14 mmol), bromobenzene at 6 g (38.21 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then stirred at ambient temperature for 60 minutes. 1-phenyl-2-(1,3,5-triazin-2-yl)-1,5-dihydroimidazo[1,2-a]pyridine was obtained after a the reaction and filtering. 1-phenyl-2-(1,3,5-triazin-2-yl)-1,5-dihydroimidazo[1,2-a]pyridine at 6.95 g (25.23 mmol), BuSnCl at 8.28 g (25.43 mmol), and n-BuLi at 12.81 mg (0.20 mmol) were dissolved in 50 ml of THF, and then stirred at a temperature of −78° C. for 10 minutes. Thereafter, the was increased to ambient temperature. Bromobenzene at 6 g (38.21 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then refluxed and stirred at a temperature of 50° C. for 12 hours. The resultant was filtered, and then 9-bromo-10-phenylanthracene at 6.7 g (20.01 mmol), Pd(PPh$_3$)$_4$ at 23.1 mg (0.02 mmol), and K$_2$CO$_3$ at 2.90 g (21.0 mmol) were added thereinto. This was refluxed and stirred in a solution of 25 ml of dioxane mixed with of 25 ml of distilled water at a temperature of 160° C. for 48 hours.

After the reaction was completed, 20 ml of cold distilled water was added thereinto. Then, extraction using ethyl acetate was performed. After a drying operation using magnesium sulfate and filtering, the solvent was evaporated. Then, 10.91 g of the compound (18.08 mmol, yield 47.31%) represented by Chemical Formula 29 was obtained through column chromatography.

$^1$H NMR (300 MHz, DMSO), d (ppm): 9.26 (1H, s), 8.22-8.19 (4H, t), 7.71-7.32 (16H, m), 7.20 (1H, t), 6.58 (2H, d), 6.17 (1H), 5.60 (1H, t), 4.73 (1H, s), 3.80 (1H, d)

m/z: 332.02

Synthesis Example 6

Synthesis of Chemical Formula 33

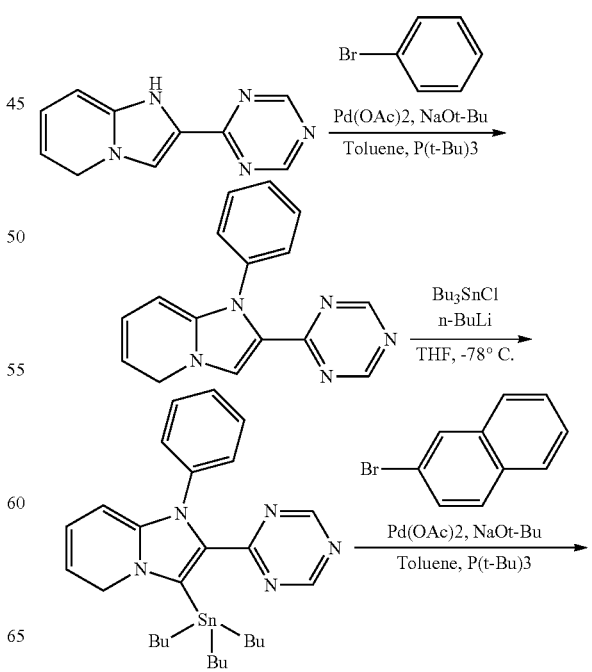

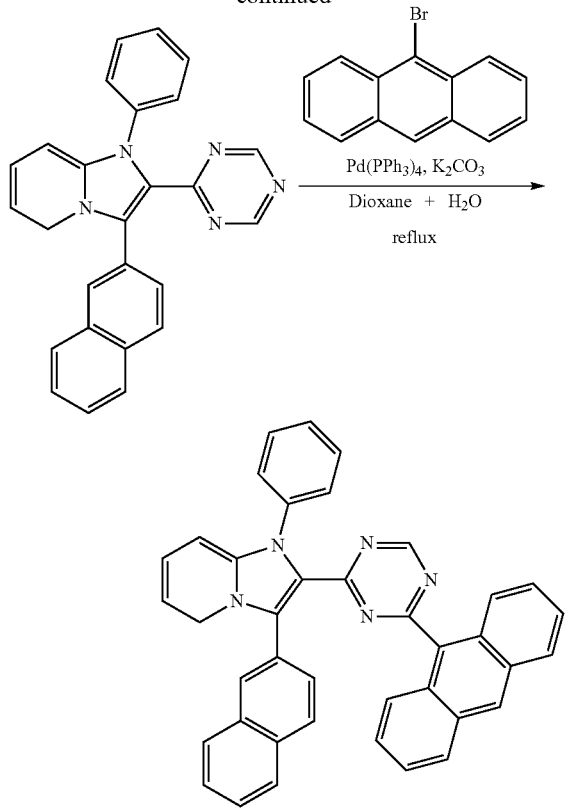

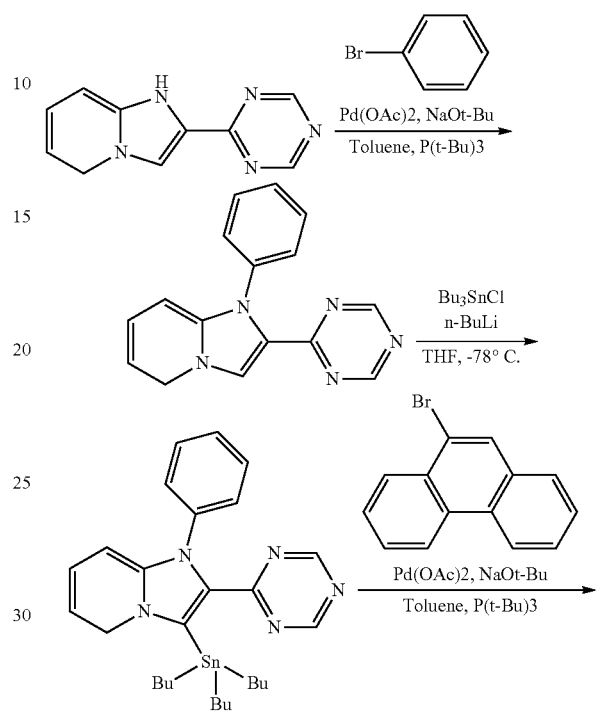

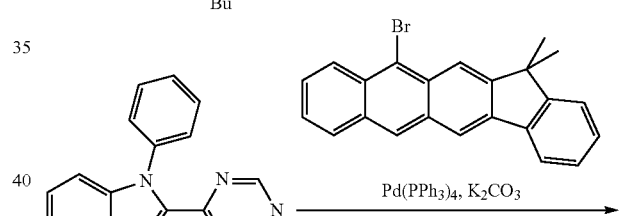

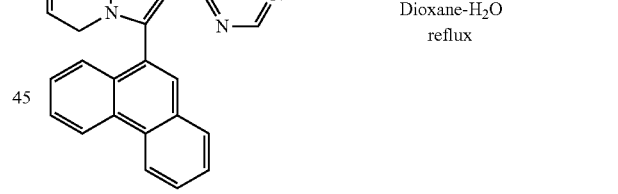

2-(1,3,5-triazin-2-yl)-1,5-dihydroimidazo[1,2-a]pyridine at 7 g (35.14 mmol), bromobenzene at 6 g (38.21 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were solved in 20 ml of toluene, and then stirred at ambient temperature for 60 minutes. 1-phenyl-2-(1,3,5-triazin-2-yl)-1,5-dihydroimidazo[1,2-a]pyridine was obtained after a the reaction and filtering. 1-phenyl-2-(1,3,5-triazin-2-yl)-1,5-dihydroimidazo[1,2-a]pyridine at 6.95 g (25.23 mmol), BuSnCl at 8.28 g (25.43 mmol), and n-BuLi at 12.81 mg (0.20 mmol) were dissolved in 50 ml of THF, and then stirred at a temperature of −78° C. for 10 minutes. Thereafter, the temperature was increased to ambient temperature. 2-bromonaphthalene at 5.75 g (27.8 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then refluxed and stirred at a temperature of 50° C. for 12 hours. The resultant was filtered, and then 9-bromoanthracene at 4.89 g (19.01 mmol), Pd(PPh$_3$)$_4$ at 23.1 mg (0.02 mmol), and K$_2$CO$_3$ at 2.48 g (18.0 mmol) were added thereinto. This was refluxed and stirred in a solution of 25 ml of dioxane mixed with 25 ml of distilled water at a temperature of 160° C. for 48 hours.

After the reaction was completed, 20 ml of cold distilled water was added thereinto. Then, extraction using ethyl acetate was performed. After a drying operation using magnesium sulfate and filtering, the solvent was evaporated. Then, 8.67 g of the compound (15.01 mmol, yield 39.27%) represented by Chemical Formula 33 was obtained through column chromatography.

$^1$H NMR (300 MHz, DMSO), d (ppm): 9.26 (1H, s), 8.55 (1H, s), 8.20 (2H, d), 8.01-7.95 (4H, m), 7.85-7.84 (3H, m), 7.53-7.47 (6H, m), 7.32 (2H, t), 7.20 (1H, t), 6.58 (2H, d), 6.17 (1H, d), 5.60 (1H, t), 4.73 (1H, s), 3.80 (1H, d)

m/z: 577.23

Synthesis Example 7

Synthesis of Chemical Formula 37

2-(1,3,5-triazin-2-yl)-1,5-dihydroimidazo[1,2-a]pyridine at 7 g (35.14 mmol), bromobenzene at 6 g (38.21 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then stirred at ambient temperature for 60 minutes. 1-phenyl-2-(1,3,5-triazin-2-yl)-1,5-dihydroimidazo[1,2-a]pyridine was obtained after a the reaction and filtering. 1-phenyl-2-(1,3,5-triazin-2-yl)-1,5-dihydroimidazo[1,2-a]pyridine at 6.95 g (25.23 mmol), BuSnCl at 8.28 g (25.43 mmol), and n-BuLi at 12.81 mg (0.20 mmol) were dissolved in 50 ml of THF, and then stirred at a temperature of −78° C. for 10 minutes. Thereafter, the temperature was increased to ambient temperature. 9-bromophenanthrene at 5.86 g (22.8 mmol), Pd(OAc)$_2$ at 44.9 mg (0.2 mmol), NaOt-Bu at 19.22 mg (0.20 mmol), and P(t-Bu)$_3$ at 38.37 mg (0.19 mmol) were dissolved in 20 ml of toluene, and then refluxed and stirred at a temperature of 50° C. for 12 hours. The resultant was filtered, and then 2-bromonaphthalene at 3.73 g (18.01 mmol), Pd(PPh$_3$)$_4$ at 23.1 mg (0.02 mmol), and K$_2$CO$_3$ at 2.48 g (18.0 mmol) were added thereinto. This was refluxed and stirred in a solution of 25 ml of dioxane mixed with 25 ml of distilled water at a temperature of 160° C. for 48 hours.

After the reaction was completed, 20 ml of cold distilled water was added thereinto. Then, extraction using ethyl acetate was performed. After a drying operation using magnesium sulfate and filtering, the solvent was evaporated. Then, 8.92 g of the compound (11.99 mmol, yield 31.37%) represented by Chemical Formula 37 was obtained through column chromatography.

$^1$H NMR (300 MHz, DMSO), d (ppm): 9.26 (1H, s), 8.98 (1H, d), 8.84 (1H, d), 8.41 (1H, s), 8.24-8.20 (2H, m), 8.11-8.10 (2H, m), 8.01 (1H, d), 7.92-7.90 (2H, m), 7.75-7.32 (12H, m), 7.20 (1H, t), 6.58 (1H, d), 6.17 (1H, d), 5.60 (1H, t), 4.73 (1H, s), 3.80 (1H, d), 1.75 (2H, s)

m/z: 743.30

For the compounds other than the aforementioned compounds, their synthesis methods may be understood by referring to the synthesis method and raw materials.

TEST EXAMPLES

Test Example 1

As the anode, a 15 Q/cm$^2$ 500 Å ITO glass substrate (available from Dow Corning Corporation) was cut to dimensions of 50 mm×50 mm×0.5 mm and was subjected to an ultrasonic wave cleaning process for about one minute using isopropyl alcohol and pure water, and ultraviolet ray irradiation for about one minute. Then, the glass substrate was exposed to ozone to be cleaned and installed in a vacuum deposition apparatus. First, 2-TNATA (4,4',4"-tris (N-(2-naphthyl)-N-phenyl-amino)-triphenylamine) was subjected to vacuum deposition to form an HIL having a thickness of 600 Å on top of the substrate. Then, NPB (N,N'-bis(naphthalen-1-yl)-N,N'-bis(phenyl)-benzidine), serving as a hole transport compound, was subjected to vacuum deposition to a thickness of 300 Å to form a hole transport layer.

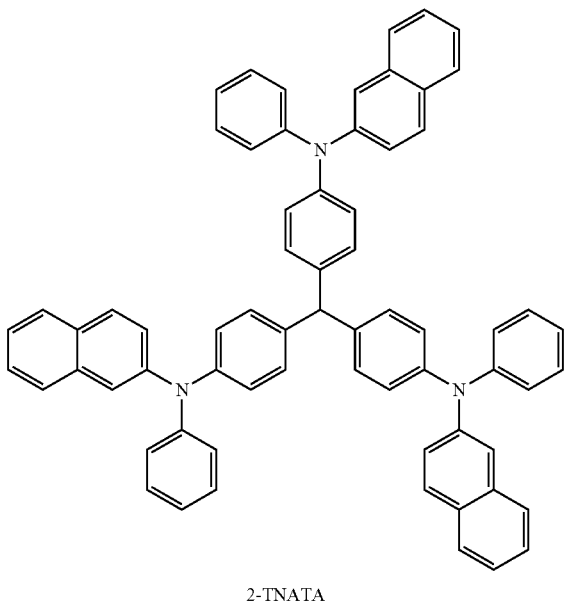

2-TNATA

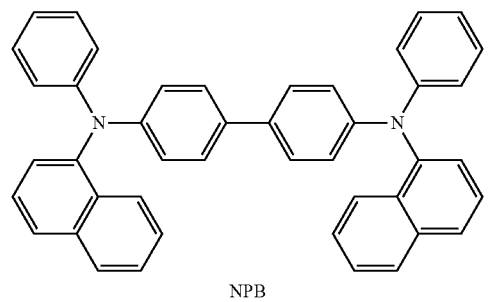

NPB

Next, blue host ADN (9,10-di(naphth-2-yl)anthracene) and DNTPD (N1,N1'-(biphenyl-4,4'-diyl)bis(N1-phenyl-N4,N4-di-mtolylbenzene-1,4-diamine) were simultaneously subjected to vacuum deposition in a weight ratio of 96:4 to form an emission layer having a thickness of 300 Å on top of the hole transport layer. Then, the compound represented by Chemical Formula 11, below, was subjected to vacuum deposition to a thickness of 300 Å to form an electron transport layer on top of the emission layer. Thereafter, Al was subjected to vacuum deposition to a thickness of 1,200 Å (cathode electrode) to thereby manufacture an organic light emitting diode device.

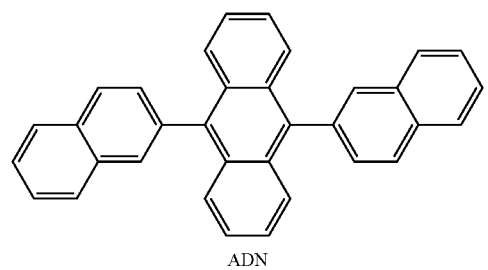 [SMILES: c1ccc2cc(-c3c4ccccc4c(-c4ccc5ccccc5c4)c4ccccc34)ccc2c1]

ADN

-continued

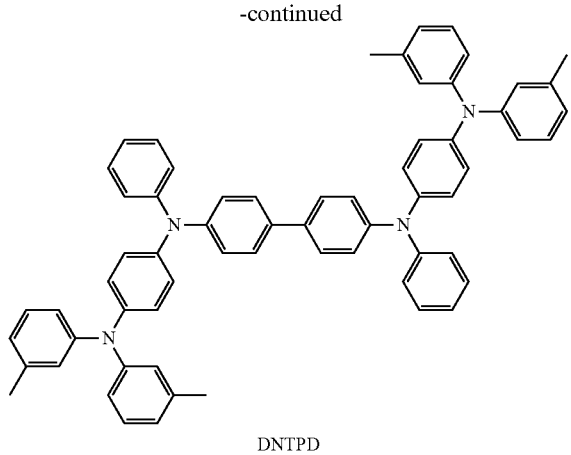

DNTPD

Chemical Formula 11

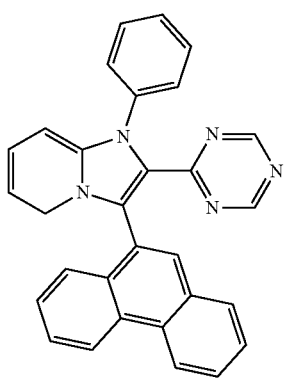

Test Example 2

An organic light emitting diode device was manufactured by using substantially the same method as that of Test Example 1, except that the compound represented by Chemical Formula 16, below, was used to form the electron transport layer instead of the compound represented by Chemical Formula 11.

Chemical Formula 16

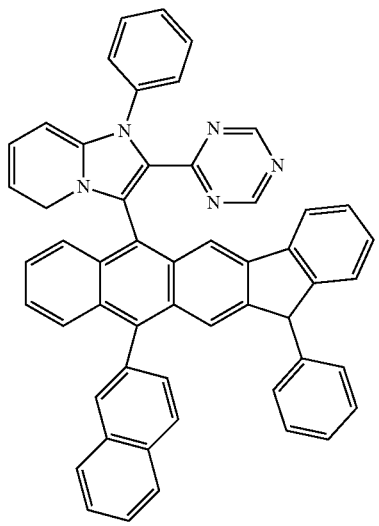

Test Example 3

An organic light emitting diode device was manufactured by using substantially the same method as that of Test Example 1, except that the compound represented by Chemical Formula 22, below, was employed to form the electron transport layer instead of the compound represented by Chemical Formula 11.

Chemical Formula 22

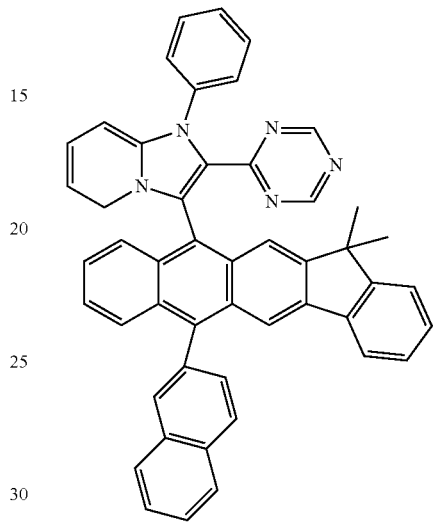

Test Example 4

An organic light emitting diode device was manufactured by using substantially the same method as that of Test Example 1, except that the compound represented by Chemical Formula 29, below, was employed to form the electron transport layer instead of the compound represented by Chemical Formula 11.

Chemical Formula 29

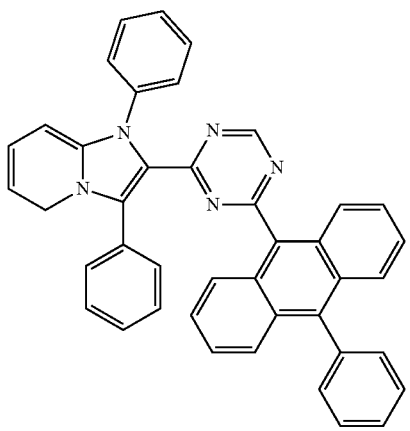

Test Example 5

An organic light emitting diode device was manufactured by using substantially the same method as that of Test Example 1, except that the compound represented by Chemical Formula 33, below, was employed to form the electron transport layer instead of the compound represented by Chemical Formula 11.

Chemical Formula 33

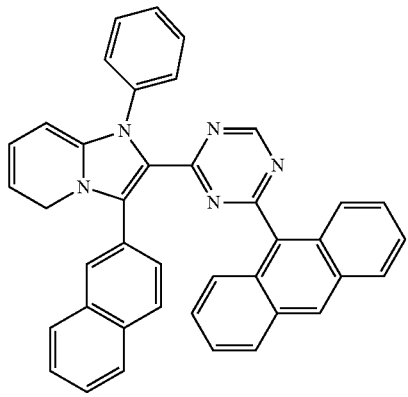

Test Example 6

An organic light emitting diode device was manufactured by using substantially the same method as that of Test Example 1, except that the compound represented by Chemical Formula 37 was employed to form the electron transport layer instead of the compound represented by Chemical Formula 11.

Chemical Formula 37

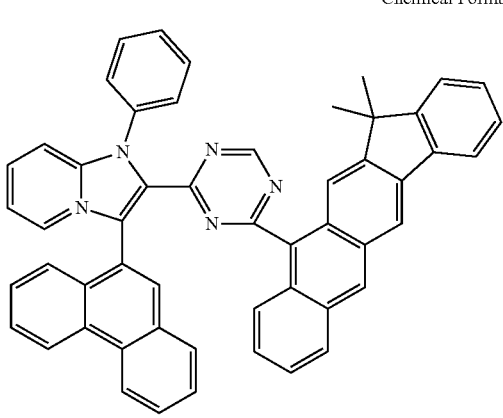

Comparative Example 1

An organic light emitting diode device was manufactured by using substantially the same method as that of Test Example 1, except that Alq$_3$ (tris(8-hydroxy-quinolinato) aluminum) was employed to form the electron transport layer instead of the compound represented by Chemical Formula 11.

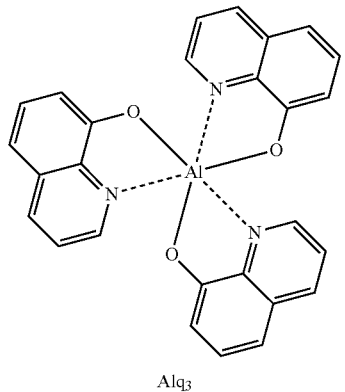

Alq$_3$

Evaluation

The characteristics of the organic light emitting diode device according to Test Examples 1 to 6 and Comparative Example 1 were evaluated.

The results are shown in Table 1, below.

TABLE 1

|  | Electron transport layer material | Voltage (V) | Efficiency (Cd/A) | Lifespan (h) (T95%) |
| --- | --- | --- | --- | --- |
| Test Example 1 | Chemical Formula 11 | 5.2 | 5.1 | 368 |
| Test Example 2 | Chemical Formula 16 | 5.4 | 5.1 | 343 |
| Test Example 3 | Chemical Formula 22 | 5.7 | 4.9 | 284 |
| Test Example 4 | Chemical Formula 29 | 5.6 | 5.8 | 337 |
| Test example 5 | Chemical Formula 33 | 5.3 | 5.2 | 332 |
| Test example 6 | Chemical Formula 37 | 5.6 | 5.0 | 294 |
| Comparative Example 1 | Alq3 | 6.4 | 4.8 | 243 |

(T95% indicates a time (in hours h) that it takes for the luminance to drop to 95% when the organic light emitting diode device is driven by setting an initial luminance as 100% while continuously applying a current density 0.550 mA/cm$^2$)

Referring to Table 1, it may be seen that all the characteristics of driving voltage, efficiency, and lifespan were improved in the organic light emitting diode device according to Test Examples 1 to 6, as compared to Comparative Example 1.

The embodiments may provide an organic compound that is applicable to an organic light emitting diode device.

The organic light emitting diode device including the compound according to the exemplary embodiment may have an outstanding lifespan characteristic, and may have high light emitting efficiency even in the case of using a low driving voltage.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

DESCRIPTION OF SYMBOLS

10: anode 20: cathode
30: hole transport layer 40: electron transport layer
50: emission layer 60: hole injection layer
70: electron injection layer 100: organic layer

What is claimed is:

1. A compound represented by the following Chemical Formula 1:

[Chemical Formula 1]

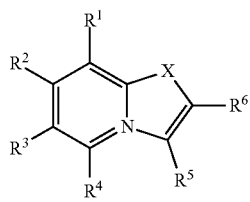

wherein, in Chemical Formula 1,
X is CRR' or NR,
R and R' are each independently hydrogen, heavy hydrogen, a substituted or unsubstituted C6 to C30 aryl group, or a substituted or unsubstituted C2 to C30 heteroaryl group,
$R^1$ to $R^4$ are each independently hydrogen, heavy hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C1 to C30 amine group, or a substituted or unsubstituted silyl group,
$R^5$ is hydrogen, heavy hydrogen, a substituted or unsubstituted C6 to C50 aryl group, a substituted or unsubstituted C2 to C50 heteroaryl group, or a substituted or unsubstituted fused ring-containing group, and
$R^6$ is hydrogen, heavy hydrogen, a substituted or unsubstituted C6 to C50 aryl group, a substituted or unsubstituted C2 to C50 heteroaryl group, a substituted or unsubstituted C1 to C30 amine group, or a substituted or unsubstituted fused ring-containing group.

2. The compound as claimed in claim 1, wherein the compound represented by Chemical Formula 1 is represented by the following Chemical Formula 2:

[Chemical Formula 2]

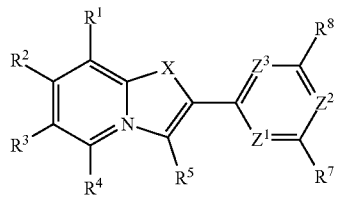

wherein, in Chemical Formula 2,
$Z^1$ to $Z^3$ are each independently CR" or N, and at least one of $Z^1$ to $Z^3$ is N, R" is hydrogen, heavy hydrogen, a substituted or unsubstituted C6 to C30 aryl group, or a substituted or unsubstituted C2 to C30 heteroaryl group,
$R^7$ and $R^8$ are each independently hydrogen, heavy hydrogen, a substituted or unsubstituted C6 to C50 aryl group, a substituted or unsubstituted C2 to C50 heteroaryl group, or a substituted or unsubstituted fused ring-containing group, and
X and $R^1$ to $R^5$ are the same as defined with respect to Chemical Formula 1.

3. The compound as claimed in claim 2, wherein at least one of $R^5$, $R^7$, and $R^8$ includes the fused ring-containing group.

4. The compound as claimed in claim 3, wherein the fused ring-containing group includes a moiety represented by one of the following Chemical Formulae "a" to "s":

[Chemical Formula a]

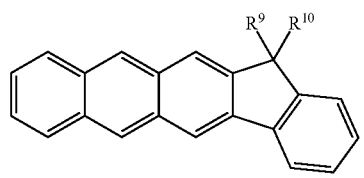

[Chemical Formula b]

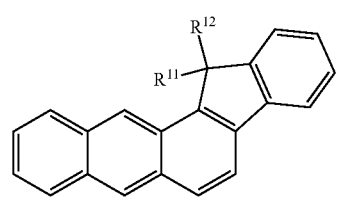

[Chemical Formula c]

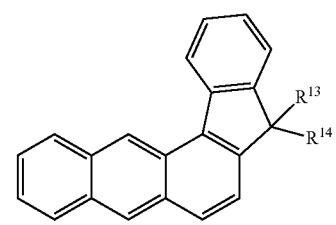

[Chemical Formula d]

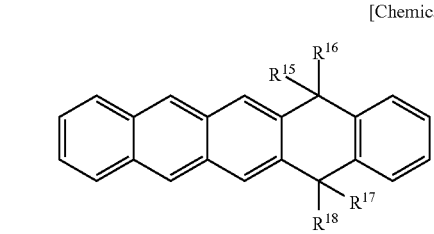

[Chemical Formula e]

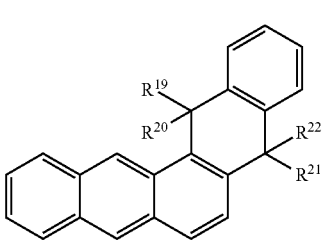

[Chemical Formula f]
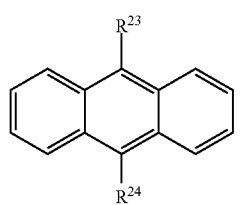

[Chemical Formula g]
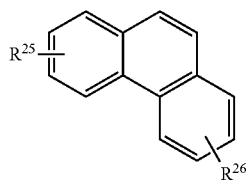

[Chemical Formula h]
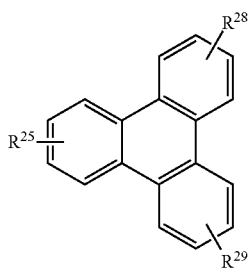

[Chemical Formula i]
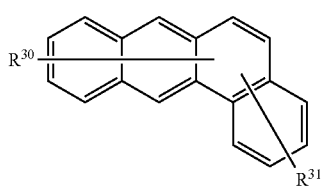

[Chemical Formula j]
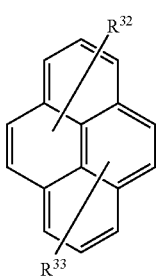

[Chemical Formula k]
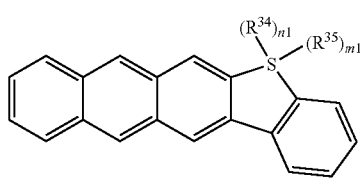

[Chemical Formula l]
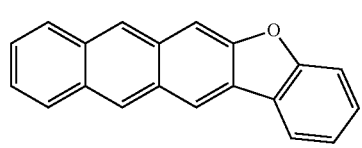

[Chemical Formula m]
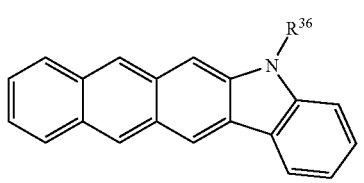

[Chemical Formula n]
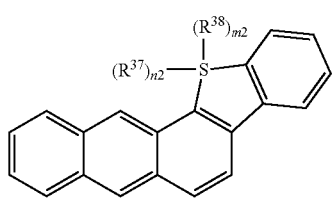

[Chemical Formula o]
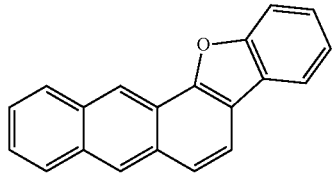

[Chemical Formula p]
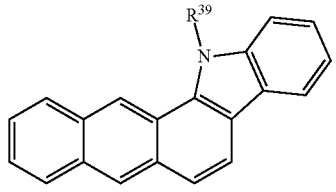

[Chemical Formula q]
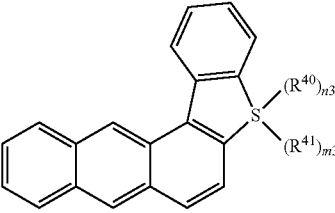

[Chemical Formula r]
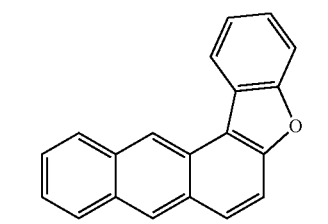

[Chemical Formula s]
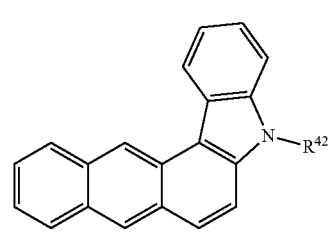

wherein, in Chemical Formulae "a" to "s", $R^9$ to $R^{42}$ are each independently hydrogen, heavy hydrogen, a substituted or unsubstituted C1 to C30 alkyl group, a substituted or unsubstituted C6 to C30 aryl group, or a substituted or unsubstituted C2 to C30 heteroaryl group, and n1, n2, n3, m1, m2, and m3 are each 0.

5. The compound as claimed in claim 1, wherein:
X is NR, and
R is a substituted or unsubstituted C6 to C30 aryl group.

6. The compound as claimed in claim 1, wherein:
$R^1$, $R^3$, and $R^4$ are hydrogen, and
$R^2$ is hydrogen or a substituted or unsubstituted C6 to C50 aryl group.

7. The compound as claimed in claim 6, wherein R² is hydrogen, a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, or a substituted or unsubstituted pyrenyl group.

8. The compound as claimed in claim 1, wherein the compound represented by Chemical Formula 1 is represented by one of the following Chemical Formulae 3 to 51:

3

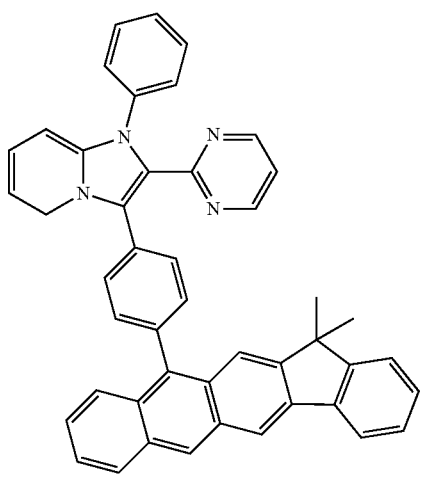

4

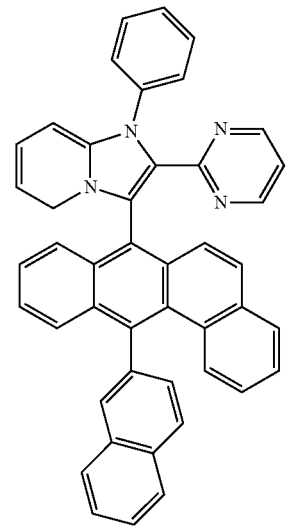

5

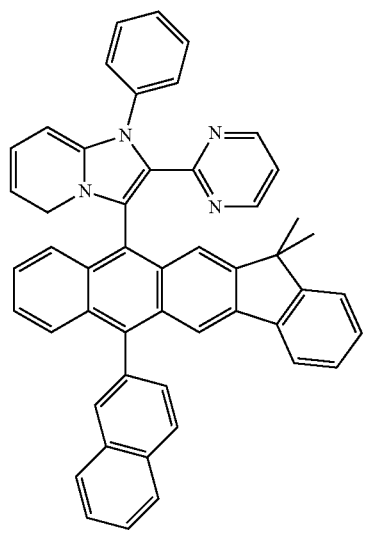

6

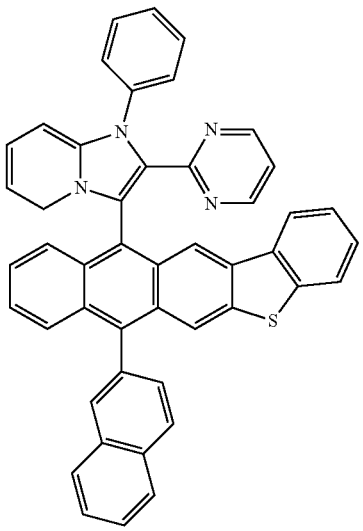

7

-continued
8
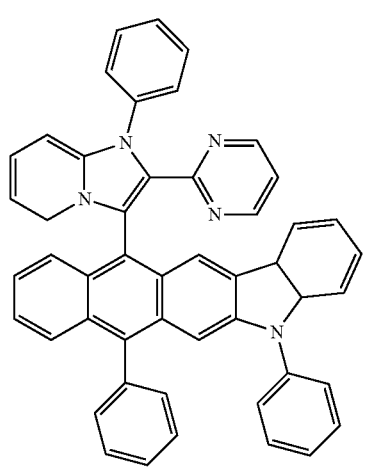
9
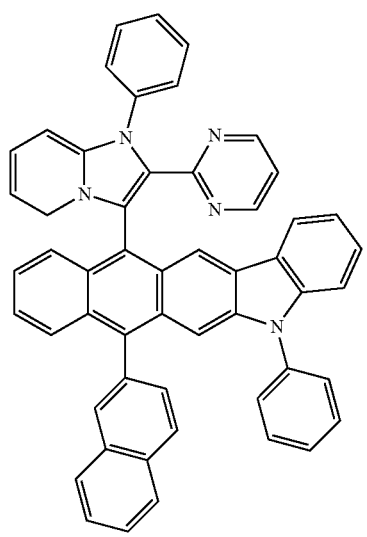
10
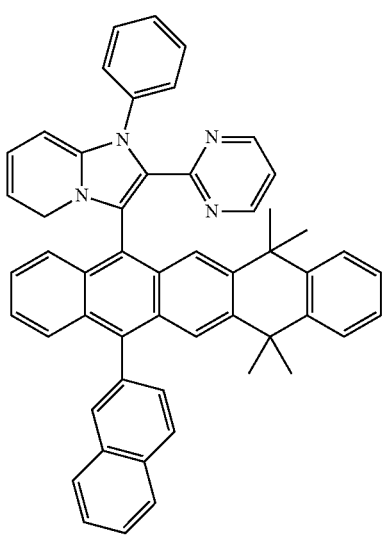
-continued
11
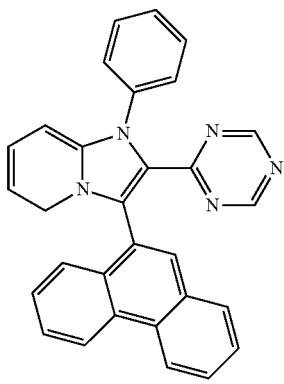
12
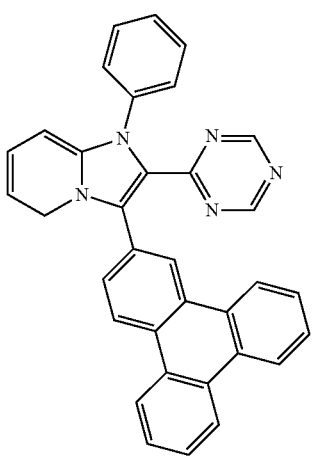
13
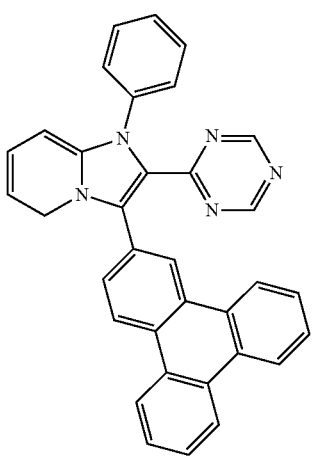

14
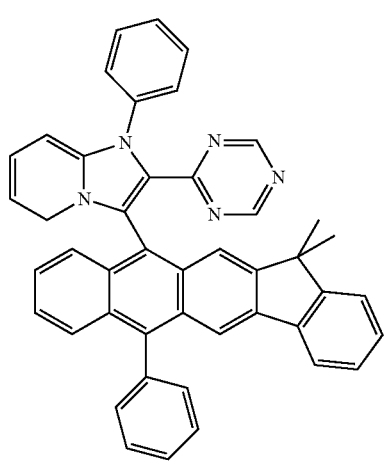
15
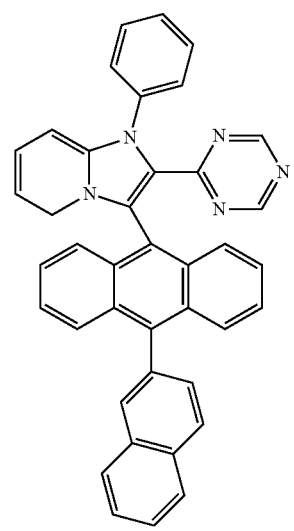
16
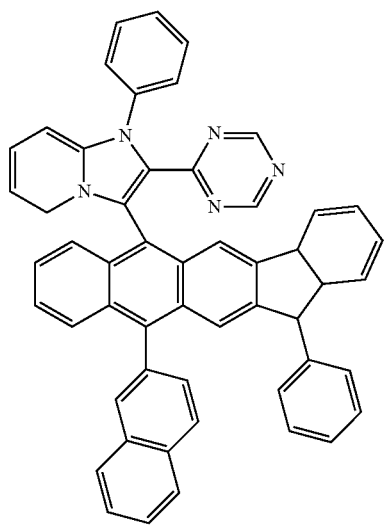
17
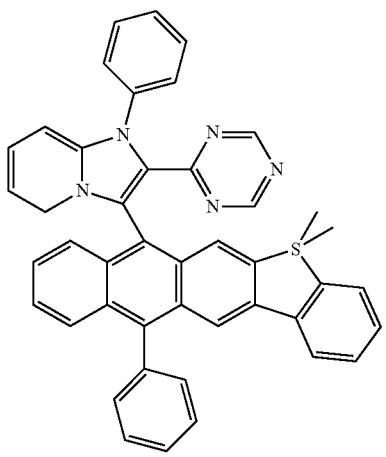
18
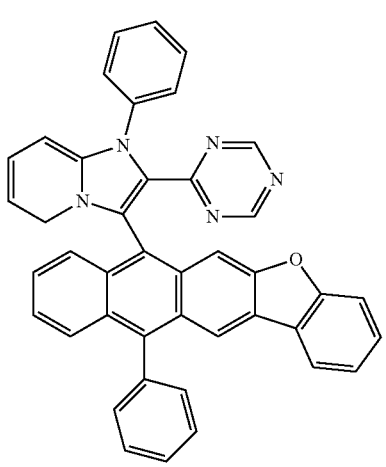
19
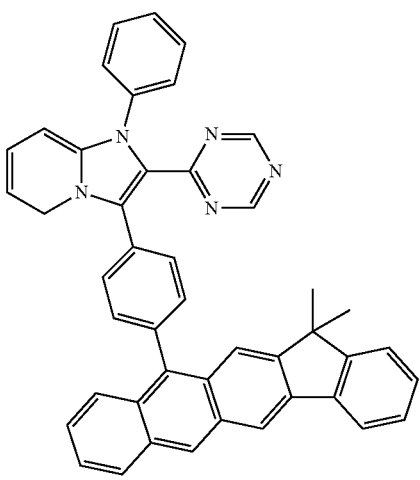

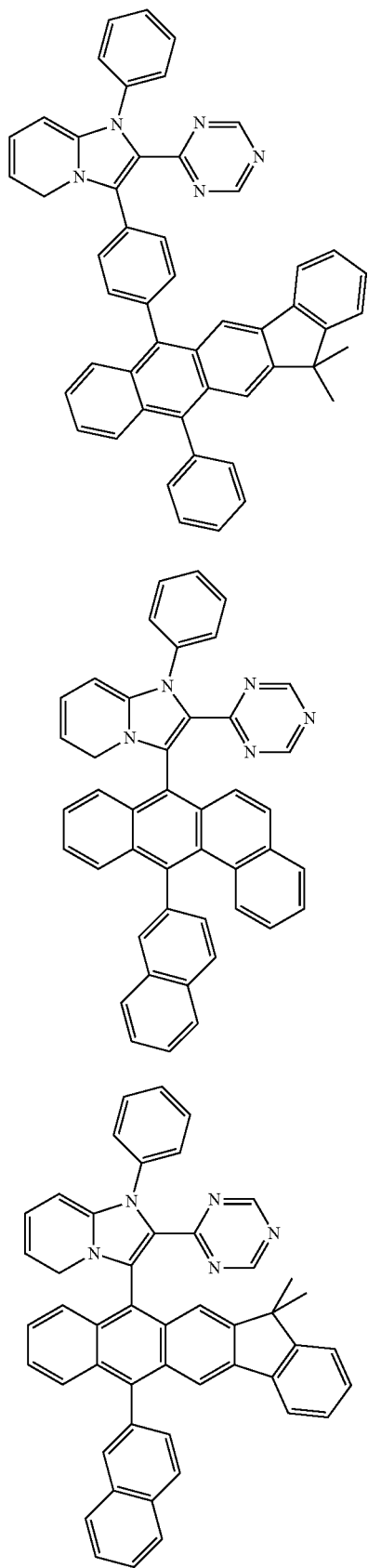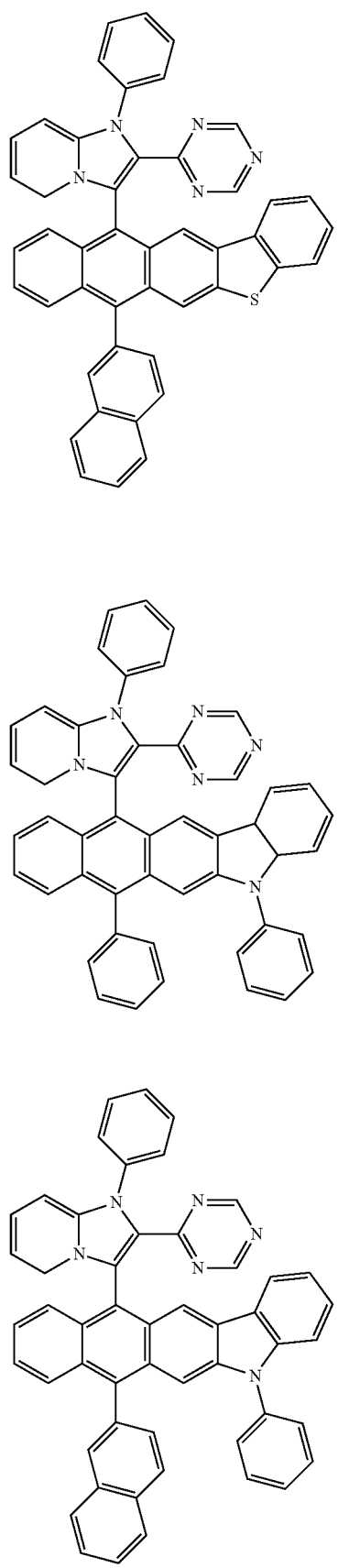

26
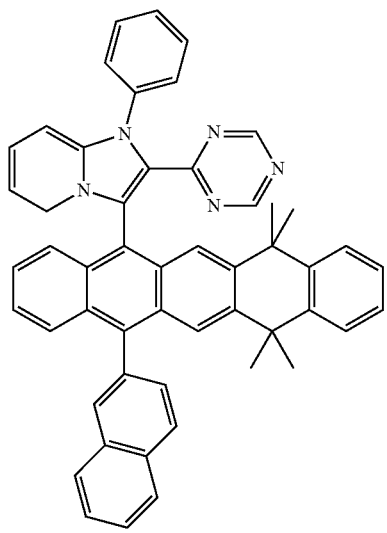
27
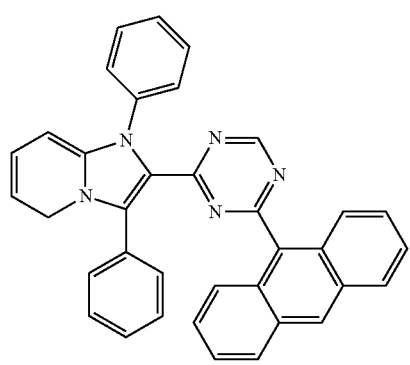
28
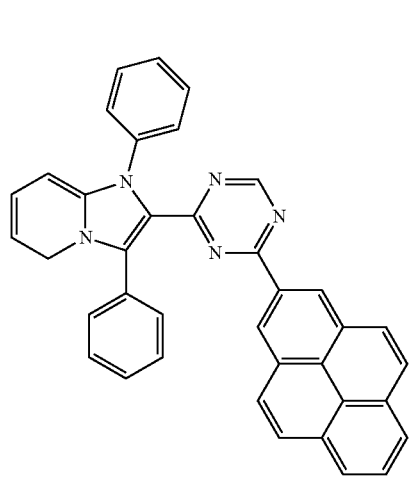
29
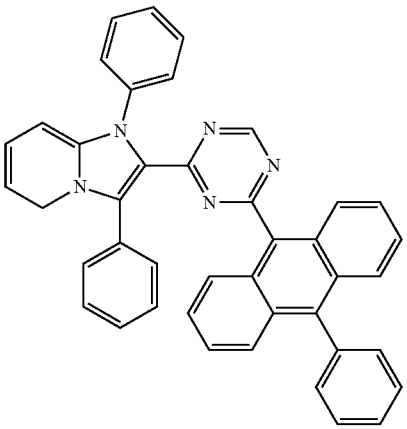
30
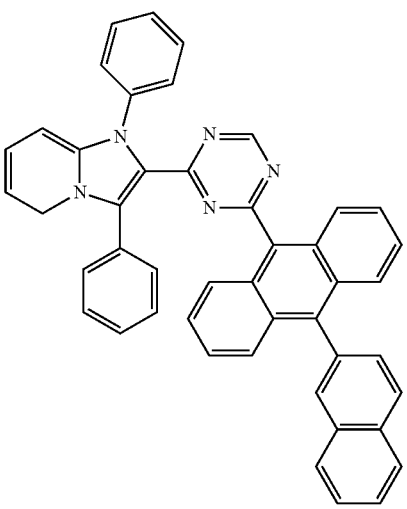
31
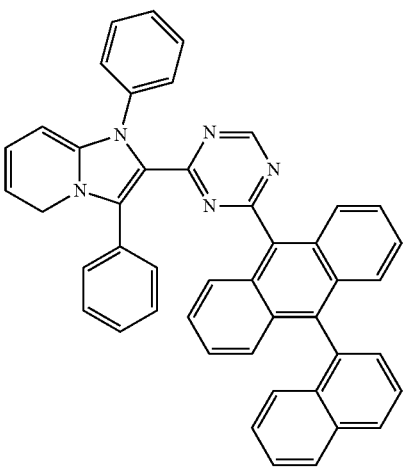

-continued
32
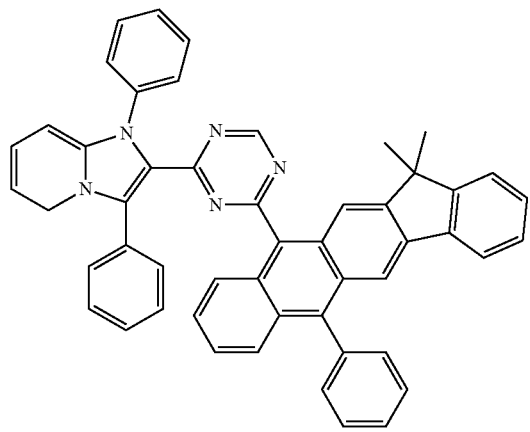
33
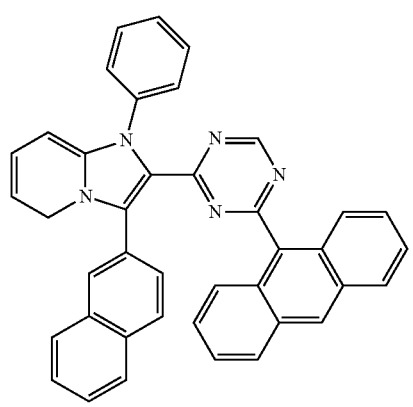
34
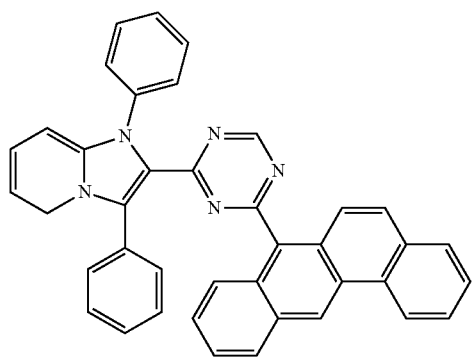
35
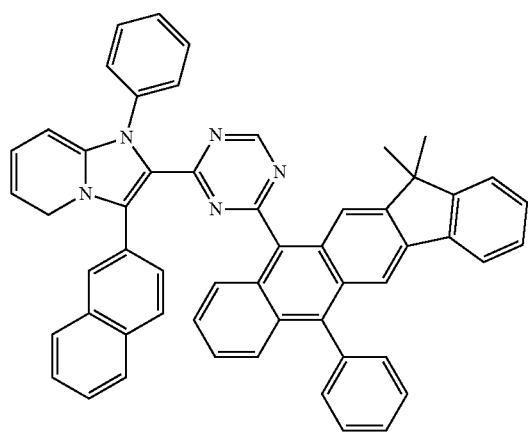
-continued
36
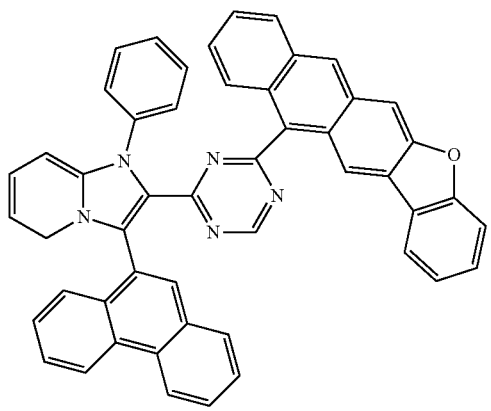
37
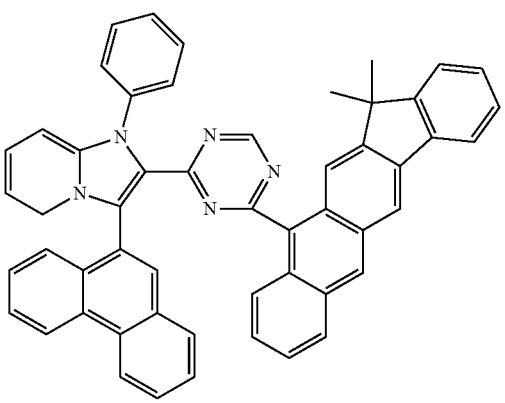
38
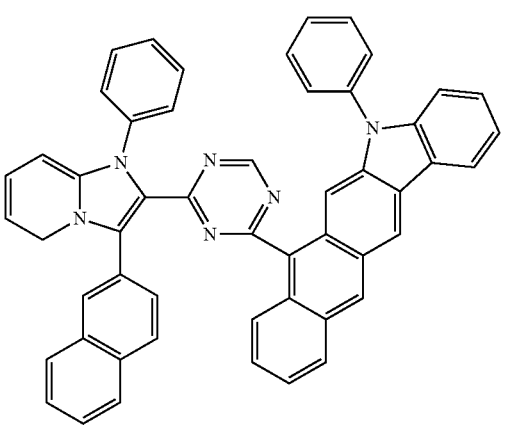
39
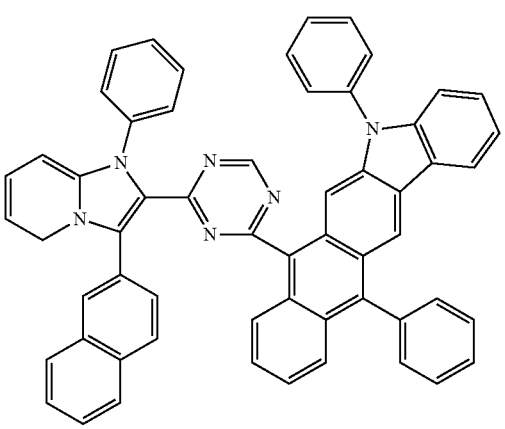

40
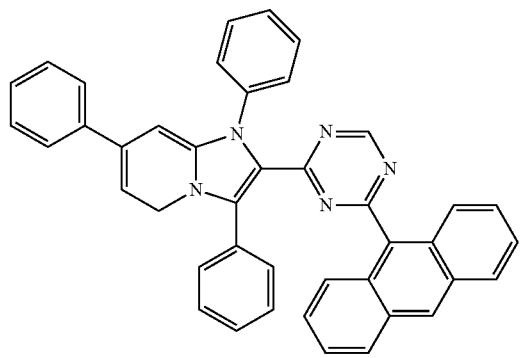
41
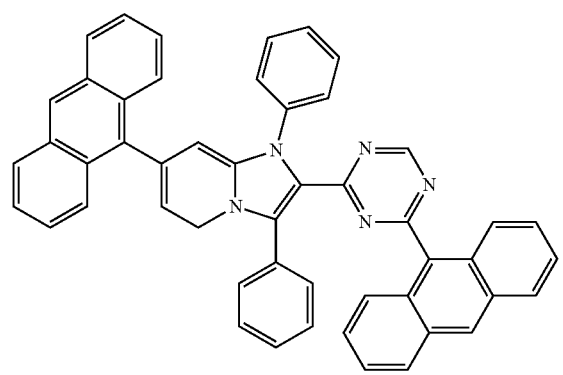
42
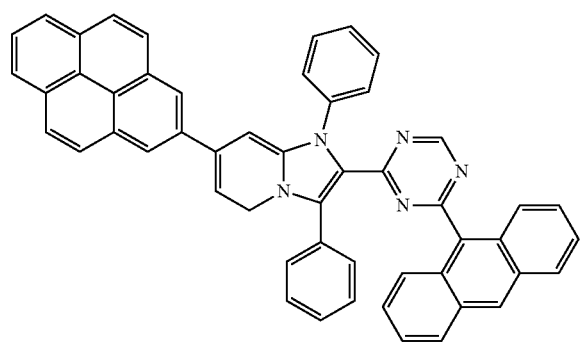
43
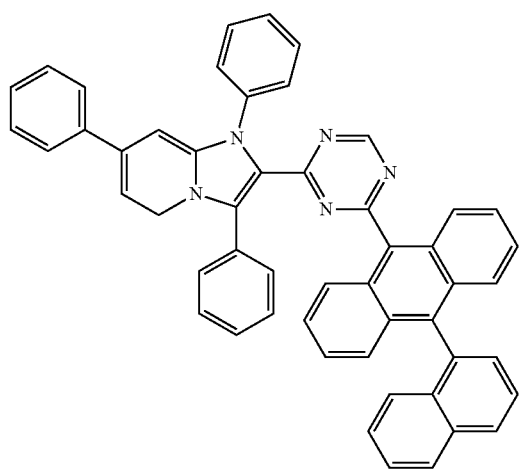
44
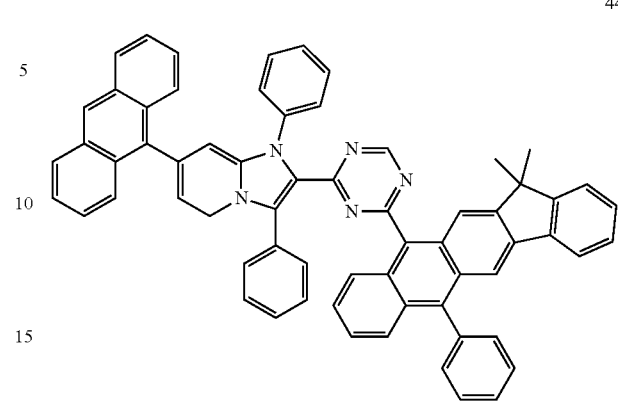
45
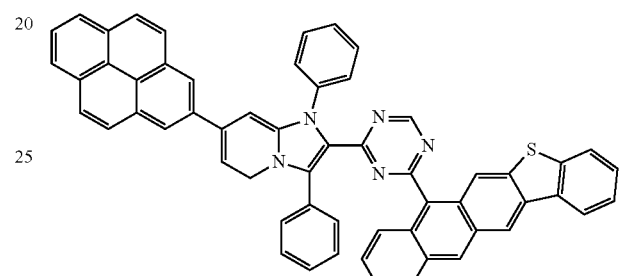
46
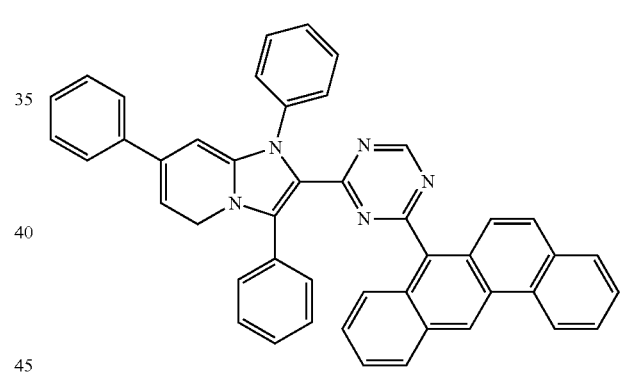
47
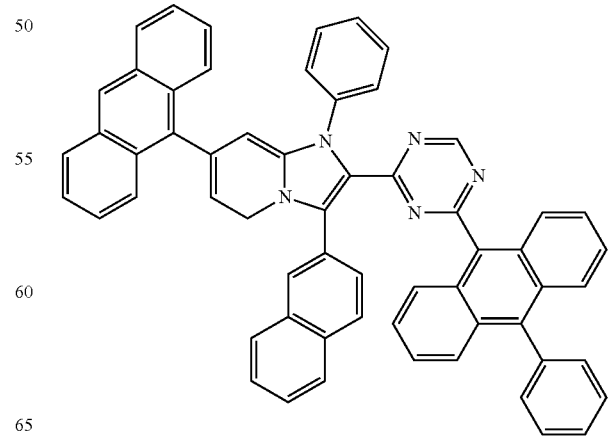

87
-continued

48

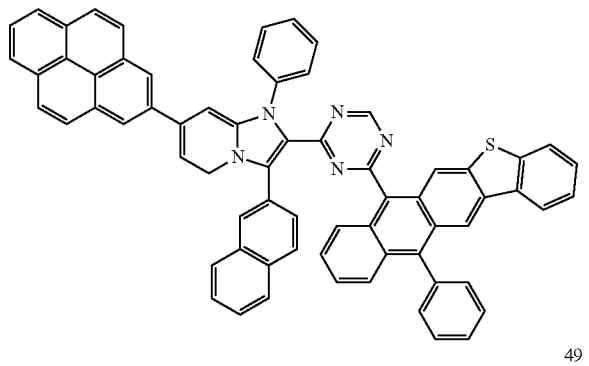

49

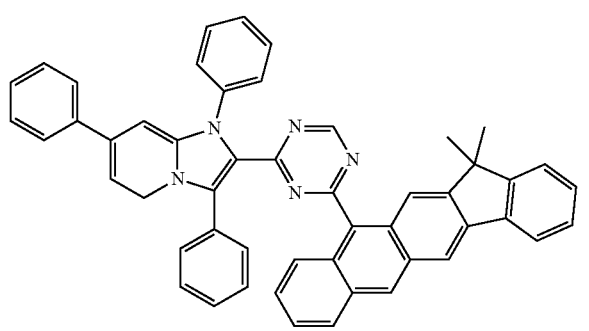

50

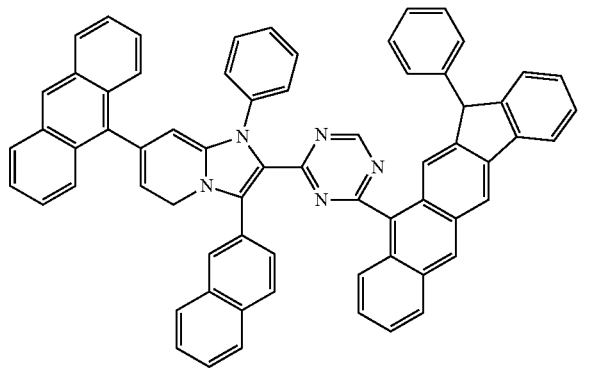

88
-continued

51

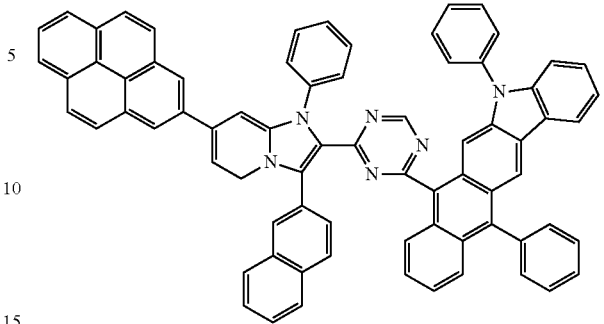

9. An organic light emitting diode device, comprising:
   an anode;
   a cathode; and
   an organic layer between the anode and the cathode,
   wherein the organic layer contains the compound according to claim 1.

10. The organic light emitting diode device as claimed in claim 9, wherein the organic layer includes an electron injection layer, an electron transport layer, a hole injection layer, a hole transport layer, or an emission layer.

11. The organic light emitting diode device as claimed in claim 9, wherein the organic layer includes an electron injection layer or an electron transport layer.

12. The organic light emitting diode device as claimed in claim 11, wherein:
   the organic layer includes the electron transport layer,
   the electron transport layer includes the compound, and
   the electron transport layer further includes a metal-containing material.

13. The organic light emitting diode device as claimed in claim 12, wherein the metal-containing material includes a Li complex.

14. A display device comprising the organic light emitting diode device according to claim 9.

* * * * *